(12) United States Patent
Eggers et al.

(10) Patent No.: US 12,035,958 B2
(45) Date of Patent: Jul. 16, 2024

(54) HEMOSTATIC SURGICAL BLADE, SYSTEM AND METHOD OF BLADE MANUFACTURE AND METHOD OF USE

(71) Applicant: Hemostatix Medical Technologies, LLC, Barlett, TN (US)

(72) Inventors: Philip E. Eggers, Dublin, OH (US); Brad Beale, Lakeland, TN (US)

(73) Assignee: Hemostatix Medical Technologies, LLC, Bartlett, TN (US)

( * ) Notice: Subject to any disclaimer, the term of this patent is extended or adjusted under 35 U.S.C. 154(b) by 662 days.

(21) Appl. No.: 17/015,609

(22) Filed: Sep. 9, 2020

(65) Prior Publication Data

US 2021/0077175 A1 Mar. 18, 2021

Related U.S. Application Data

(60) Provisional application No. 62/899,812, filed on Sep. 13, 2019.

(51) Int. Cl.
| | |
|---|---|
| *A61B 18/08* | (2006.01) |
| *A61B 18/00* | (2006.01) |
| *A61B 18/14* | (2006.01) |

(52) U.S. Cl.
CPC ............ *A61B 18/082* (2013.01); *A61B 18/14* (2013.01); *A61B 2018/00077* (2013.01); *A61B 2018/00095* (2013.01); *A61B 2018/00107* (2013.01); *A61B 2018/00428* (2013.01); (Continued)

(58) Field of Classification Search
CPC .................. A61B 18/082; A61B 18/14; A61B 2018/00077; A61B 2018/00095; A61B 2018/00107; A61B 2018/00428; A61B 2018/00601; A61B 2018/00964
See application file for complete search history.

(56) References Cited

U.S. PATENT DOCUMENTS

| | | | |
|---|---|---|---|
| 5,308,311 A * | 5/1994 | Eggers ................. | A61B 18/082 606/29 |
| 6,208,881 B1 * | 3/2001 | Champeau ......... | A61B 18/1492 607/116 |

(Continued)

*Primary Examiner* — Joseph A Stoklosa
*Assistant Examiner* — Annie L Shoulders
(74) *Attorney, Agent, or Firm* — Emerson, Thompson & Bennett, LLC; Jerry K. Mueller, Jr.

(57) ABSTRACT

A hemostatic surgical blade is formed of five symmetrically layers. A martensitic stainless steel core with oppositely disposed faces is bonded to layers exhibiting a high thermal conductivity which, in turn, are supported by buttressing layers of austenitic stainless steel. A thin aluminum layer is deposited on one side of blade blanks to enable chemical reaction bonding to electrically insulative dielectric inks formulated for use with aluminum substrates. The blade is heated by a blade heating circuit that is manufactured by thick-film printing and firing an electrically resistive heating element layer and an electrically conductive leads on an electrically insulative dielectric layer with all layers subsequently covered by a thick-film printed electrically insulative dielectric overcoat. Tissue contacting portions of blade are coated with a very thin non-stick coating. The surgical blade operates at a temperature below the threshold for pyrolysis and/or thermal decomposition of human tissue and body fluids.

21 Claims, 10 Drawing Sheets

(52) U.S. Cl.
CPC ............... *A61B 2018/00601* (2013.01); *A61B 2018/00964* (2013.01); *A61B 2018/1412* (2013.01)

(56) References Cited

U.S. PATENT DOCUMENTS

| | | | |
|---|---|---|---|
| 6,905,497 B2* | 6/2005 | Truckai | A61B 18/1442 606/49 |
| 2002/0111622 A1* | 8/2002 | Khandkar | A61B 18/14 606/45 |
| 2009/0112200 A1* | 4/2009 | Eggers | A61B 17/3211 606/29 |
| 2015/0209103 A1* | 7/2015 | Artale | A61B 18/1206 606/42 |
| 2020/0164115 A1* | 5/2020 | Murano | A61L 31/14 |

* cited by examiner

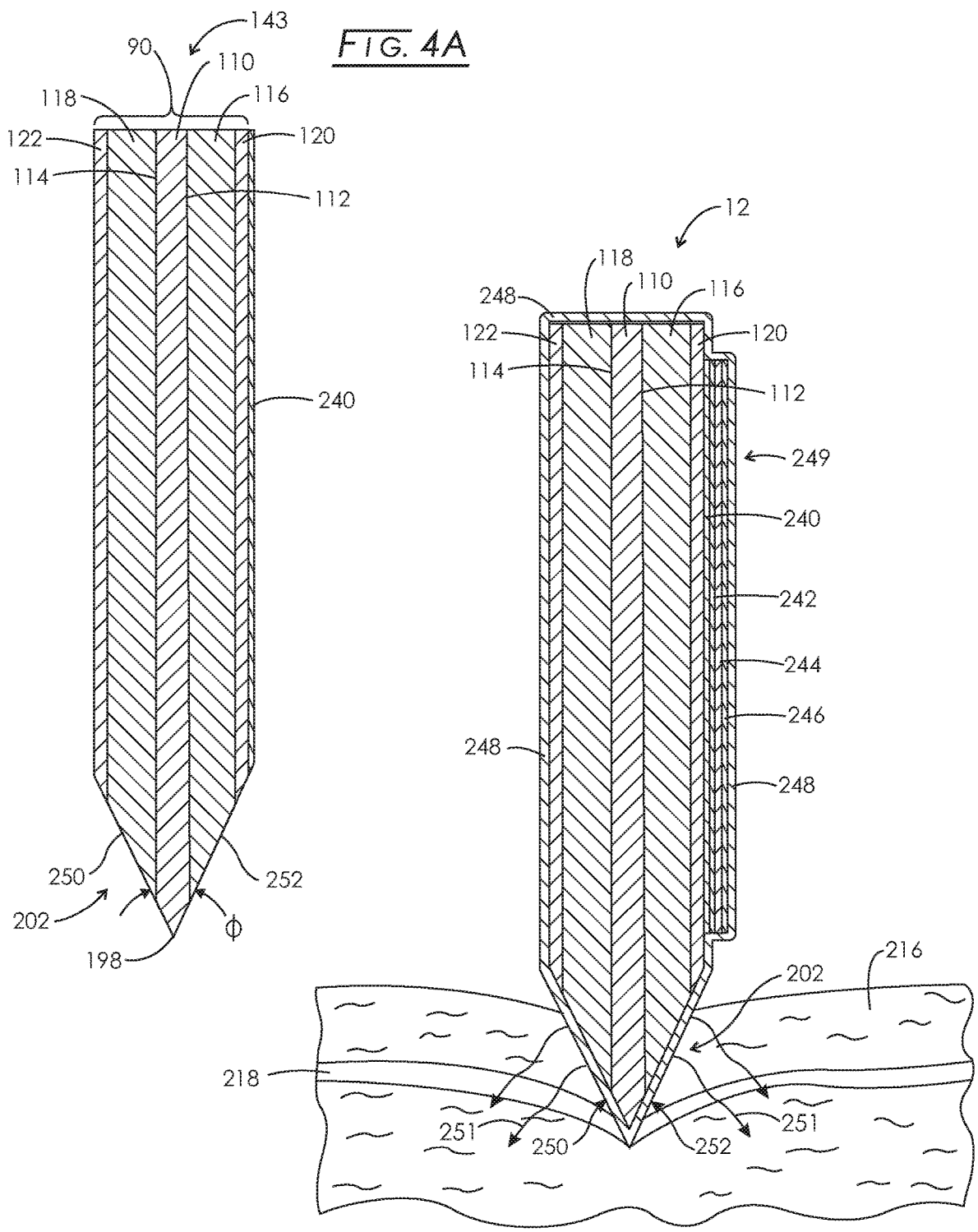

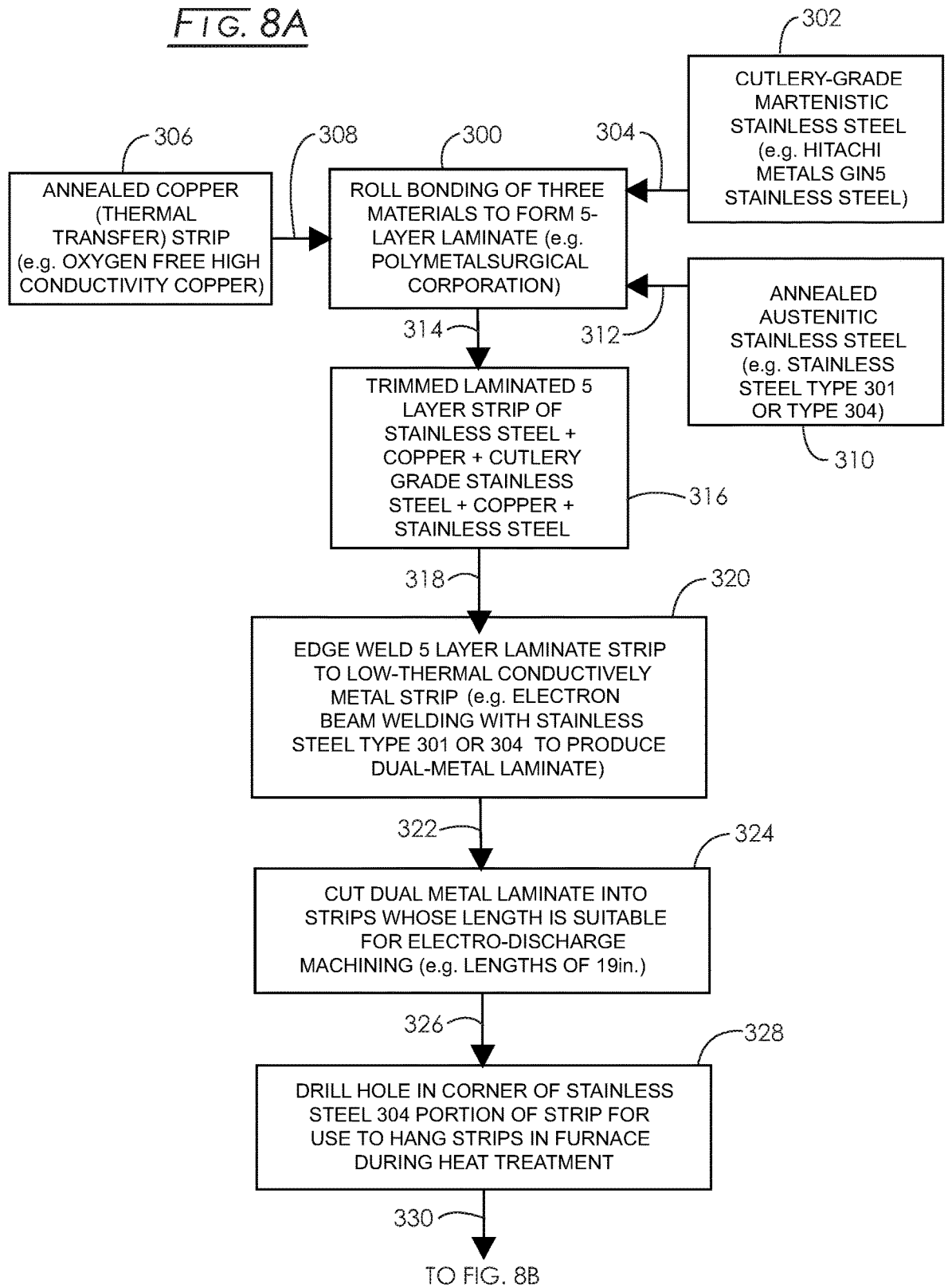

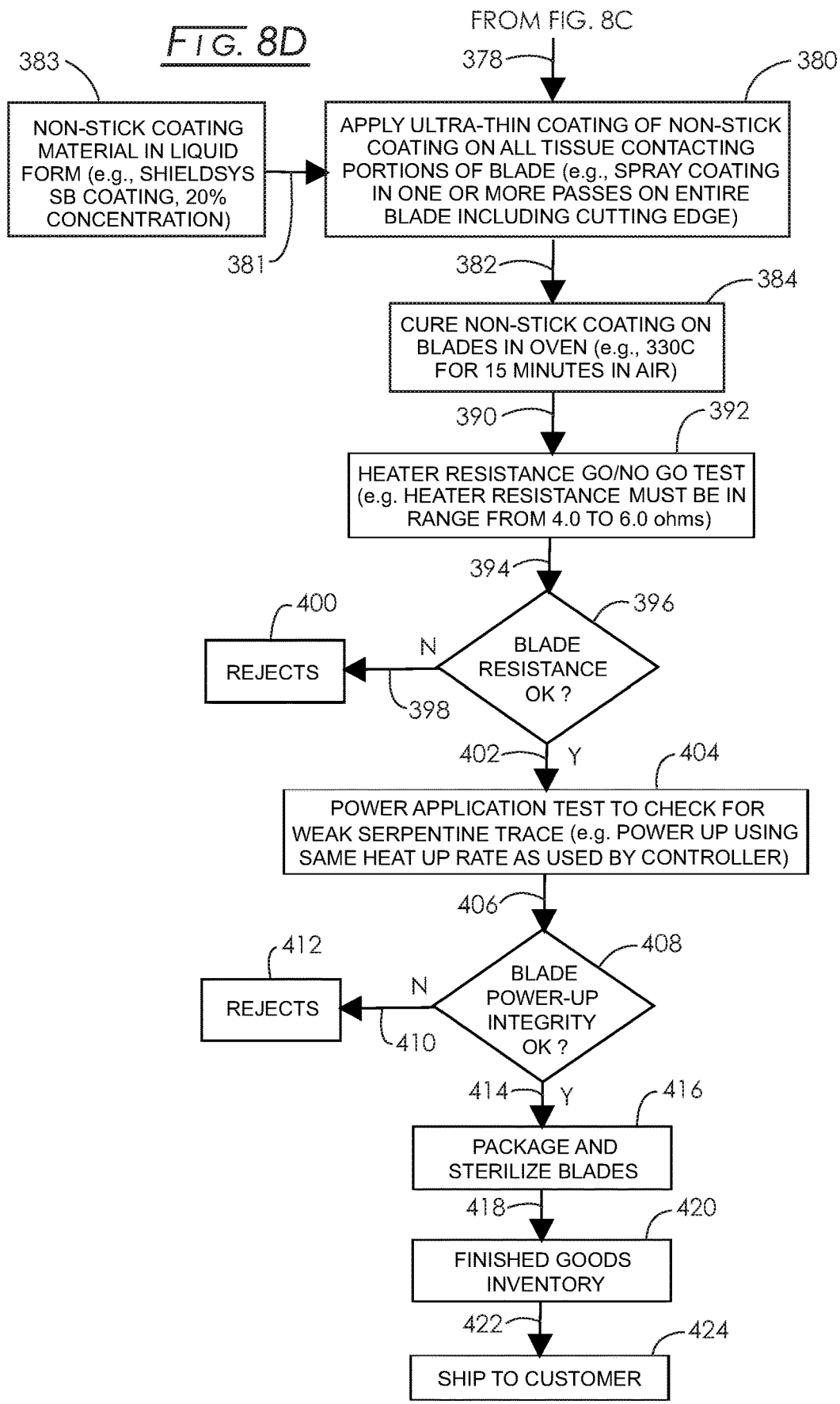

HEMOSTATIC SURGICAL BLADE, SYSTEM AND METHOD OF BLADE MANUFACTURE AND METHOD OF USE

CROSS-REFERENCE TO RELATED APPLICATIONS

This application claims benefit of U.S. provisional 62/899,812 filed on Sep. 13, 2019, the disclosure of which is expressly incorporated herein by reference.

STATEMENT REGARDING FEDERALLY SPONSORED RESEARCH AND DEVELOPMENT

Not applicable.

THE NAMES OF THE PARTIES TO A JOINT RESEARCH AGREEMENT

Not applicable.

REFERENCE TO A "SEQUENCE LISTING," A TABLE, OR A COMPUTER PROGRAM

Not applicable.

STATEMENT REGARDING PRIOR DISCLOSURES BY THE INVENTOR OR A JOINT INVENTOR

Not applicable.

BACKGROUND OF THE INVENTION

The control of bleeding during surgery accounts for a major portion of the time involved in an operation. In particular, bleeding that occurs when tissue is incised obscures the surgeon's vision, delays the operation, and reduces the precision of cutting.

One technique for minimizing the bleeding of tissue as it is being severed is known as hemostatic surgery. This technique uses a heated instrument to contact bleeding tissue. The heat is transferred from the instrument to the incised (or torn) tissue to thermally reform collagen, thereby producing a thin collagenous film that seals over the severed blood vessels and capillaries, thereby reducing bleeding. Because heat is applied locally to tissue that contacts the heated region of the instrument, there is little tissue necrosis or damage that, if present, would retard healing.

One such hemostatic instrument is known as a hemostatic surgical scalpel. This scalpel has a sharp cutting edge similar to that of a conventional steel surgical blade, and a heating element proximate to the cutting edge to heat the blade. During cutting, the surgical blade is heated and the heat is transferred to the tissue being cut.

One commercial device using this technique is a hemostatic scalpel manufactured and sold by Hemostatix Medical Technologies, Bartlett, Tennessee and described in U.S. Pat. Nos. 3,768,482, 4,481,057, 4,485,810 and 5,308,311. This device uses a multi-segmented resistive heating element whereby the current flowing through each segment is individually controlled to maintain each segment, and hence the blade, within a narrow range of user-selected temperatures.

A drawback of previously known hemostatic heated surgical blades has been the inability to deliver an adequate quantity of heat in close proximity to the cutting edge, to maintain a sharp durable cutting edge, and to be usable for sustained surgery under a wide variety of surgical cutting applications. Sufficient thermal delivery is critical to seal promptly the blood vessels and capillaries being severed. The quantity of heat that must be delivered increases with the rate at which the scalpel is being moved through the tissue and the degree of vascularization of the tissue. These conditions have limited the cutting rate and depth that the previously known devices can be used to hemostatically cut tissue.

Good surgical blades are commonly made of hard materials, such as steels and martensitic stainless steels, but these materials generally have low thermal conductivity. High thermal conductivity materials are desirable for delivering the necessary heat, but typically do not maintain a sharp and durable cutting edge. Contact of the high thermal conductivity blades with the corrosive biological fluids and operation at elevated temperatures combine to dull the cutting edges of such blades prematurely. Moreover, they also conduct large amounts of heat to the handle of the blade, making it uncomfortable for the surgeon to hold the instrument during surgery.

Attempts to use other blade materials have been made without any apparent success, e.g., ceramic blades as described in Shaw U.S. Pat. No. 3,768,482, Johnson U.S. Pat. No. 4,219,025, Lipp U.S. Pat. No. 4,231,371, and high thermal conductivity materials treated to have hardened cutting edges as described in U.S. Pat. No. 4,770,067. These devices similarly lack the combination of desirable thermal transfer properties and a durable sharp cutting edge.

Other types of hemostatic scalpel devices having non-segmented heating elements for heating the sharp surgical blades are described in a U.S. Pat. Nos. 4,207,896, 4,091,813, and 4,185,632. The delivery of heat to surgically sharp surgical blades in contact with tissue has been significantly increased by using thick-film, glass-based dielectric, resistive heater and electrical lead layers printed on the metallic blade as described in U.S. Pat. Nos. 5,308,311, 8,142,425 and 8,475,444. However, this approach requires heating the blade to greater than 400° C. for up to 60 minutes to melt and adhere the multiple thick-film printed glass dielectric, heater and lead layers. This necessary processing time at temperatures unavoidable reduces the hardness of the cutting edge due to the effect known as annealing or tempering. As a consequence of the reduced hardness, these surgical blades cannot reach the desired level of sharpness during the edge grinding process.

Also, the metallic blade, as described in U.S. Pat. No. 5,308,311, utilizes an alumina dispersion strengthened copper (GlidCop AL 15 manufactured by Gibraltar Industries/SCM Metals Corporation, Buffalo, NY) layer to provide the needed thermal conductance between the heater region and the cutting edge of the blade. As a result of the limitation of the manufactured length of alumina dispersion strengthened copper strip, the roll-bonding of this alumina dispersion strengthened copper to the cutting edge material is limited to short lengths of roll bonding and associated poor production yields. In addition, the price of the alumina dispersion strengthened copper is more than 20 times that of ordinary oxygen-free, high conductivity (OFHC) copper. The prior use of dispersion-strengthened copper was necessary due to the essential heat treatment of the cutting edge that involves heating the entire laminate to temperatures of over 1000° C. for more than 30 minutes. Conventional high thermal conductivity materials, such as oxygen-free high conductivity (OFHC) copper, will become completely annealed under these heat treatment conditions making them too weak to maintain the shape and flatness of the surgical blade.

The afore disclosed problems associated with manufacture of laminate hemostatic surgical blades incorporating alumina dispersion strengthened copper have been overcome through the manufacture of a symmetrical, five-layer laminar cutting portion structure with a cutlery-grade martensitic stainless steel edge forming core that maintains an improved hardness, for instance, from 57 to 63 Rockwell C. The opposed faces of this core are roll bonded with a highly thermally conductive metal that advantageously may be a pure, oxygen-free high conductivity (OFHC). These oppositely disposed copper layers are each bonded with a buttressing layer, for instance, formed of austenitic stainless steel such as a type 304. The two copper layers exhibit the same thickness and the two buttressing layers exhibit the same thickness. Thus, the laminar blade is symmetrical and, notwithstanding, slight differences of thermal coefficients of expansion, the laminar component will not warp, for example, during the heat hardening of the core or in the course of curing an outwardly disposed non-stick layer. In this regard, see U.S. Pat. Nos. 8,142,425 and 8,475,444, which are incorporated herein by reference in their entirety.

Accordingly, there is a continuing need to provide a sharp surgical blade capable of cutting with the same degree of sharpness as currently used "cold" surgical blades while delivering sufficient thermal energy to the tissue to cause hemostasis under a wide variety of operating conditions. In this regard, it is advantageous to achieve and maintain the highest level of hardness within the cutting edge material prior to the edge grinding and honing process. There is also a need to improve the final honing process to achieve a cutting edge at least as sharp as surgical blades currently used in surgery such as the "gold standard" Bard-Parker surgical blades manufactured by Bard-Parker, a division of Aspen Surgical, Caledonia, Michigan There is also a need for an improved non-stick coating on electrically heated surgical blades. Currently used biocompatible non-stick coatings (e.g., polytetra-fluorethylene particle-filled coatings, such as Xylan 8110 manufactured by Whitford Corporation, Elverson, Pennsylvania) have a minimum applied thickness of 0.0006 to 0.0008 inch due to the minimum polytetrafluoroethylene particle size within the coating matrix. In addition, the release characteristics of biocompatible, polytetrafluoroethylene-filled non-stick coatings, such as Xylan 8110, rapidly degrade when exposed to tissue and blood at preferred maximum heated surgical blade temperature of 300 C. Due to the minimum coating thickness averaging about 0.0007 inch, generally being applied by air-gun spraying methods, the entire length of the cutting edge region of each blade must be carefully wiped to remove the applied non-stick coating prior to final oven curing. The removal of the relatively thick layer of non-stick coating deposited at the tip of the cutting edge must be removed to avoid significant reductions in the sharpness of the cutting edge that would otherwise prevent the intended incision of soft tissue in the body of the patient.

Also, currently used polytetrafluoroethylene particle-filled non-stick coatings, such as Xylan 8110, exhibit a very low thermal conductivity of about 0.0025 watts/cm-C. At this low level of thermal conductivity, the temperature difference between the heated surgical blade supporting the non-stick coating and the surface of the non-stick coating can be as much as 51 C at a typical heat dissipation level of 25 watts and tissue contact surface area.

In addition, previously available thick-film printable, glass-based dielectric, resistive heater and electrical lead layers that are compatible with the austenitic stainless steel that forms the buttressing layer on the laminate blades are disadvantageous since they are available from only a single source, are very expensive and exhibit lower manufacturing yields and heater reliability due to line-width variations during the thick-film printing and firing processes.

The rapidly growing field of high-efficiency lighting incorporating solid-state light emitting diode (LED) light sources has created the need for dissipating highly concentrated heat loads generated within the LED. Only a few metals, notably aluminum and high aluminum containing alloys, offer a sufficiently high thermal conductivity to enable adequate dissipation of the highly concentrated heat loads associated with light emitting diodes. To address this need, several manufacturers have developed screen-printable, thick-film dielectric inks and thick-film conductor inks for producing LEDs that [a] can be fired in air at temperatures below the melting point of aluminum heat sinks, [b] reactively bond with aluminum to assure good adherence to the aluminum heat sink and [c] provide a thermal coefficient of expansion sufficiently close to that of aluminum heat sinks to withstand repeated thermal cycling with rapid rates of heat-up upon the sudden "turn-on" application of power to the LED. By way of example, thick-film dielectric inks and thick-film conductor inks suitable for screen printing and firing on aluminum heat sinks are commercially available from DuPont Microcircuit Materials (Research Triangle Park, North Carolina) and Heraeus Electronics (Hanau, Germany).

Yet another approach to thick-film printing conductor and resistor inks on aluminum substrates involves the deposition of aluminum oxide onto the surface of an aluminum heat sink using plasma spraying fine aluminum oxide particles. In this regard, see the heater manufacturing method disclosed in U.S. Pat. No. 6,222,166.

It is an object of the present invention to overcome the limitations of previous thick-film inks, as well as methods for manufacturing electrically heated, surgically sharp surgical blades.

Another prior art hemostatic surgery method for minimizing bleeding in human tissue, as it is being severed, is known as electrosurgery. Electrosurgery has been widely used in surgery since its invention in the 1931 by William Bovie (see U.S. Pat. No. 1,813,902). The term electrosurgery (also called radiofrequency surgery) refers to the passage of high-frequency electrical current through tissue in order to achieve specific surgical effects, such as, cutting and coagulation of transected blood vessels. A monopolar electrosurgical device consists of a high frequency electrical generator and two electrodes. A high frequency electrical current of at least about 300 kHz is used in monopolar electrosurgery, since the electrical impedance of human tissue approaches a minimum at frequencies of 300 kHz or higher. Such high-frequency alternating electric current flows from the active or treatment electrode through the patient's body and then to the return (dispersive) electrode, where current flows back to the electrosurgical generator. Adjacent to the active electrode, tissue resistance to the passage of alternating current converts electrical energy to heat, resulting in rapid tissue heating to temperatures well above the boiling point of the liquid contents of the cells that comprise all tissues. While rapid heat generation occurs within the tissue adjacent to the active or treatment electrode, the active or treatment electrode acts as a electrical conductor that only conducts the electrical current and remains cooler than the adjacent treated tissue. A sudden increase in tissue temperature above the boiling point results in rapid explosive vaporization of the water content in the tissue adjacent to the electrode. This leads to tissue fragmentation, which allows the electrode to pass through the tissue and is the mechanism of tissue cutting in monopolar electrosurgery procedures, a mechanism also known as electrosection (see Taheri, A., et. al., Electrosurgery-Part I. Basics and Principles. Journal of American Academy of Dermatology 2014; 70 [4]; 591.e1-591.e14).

In addition to the rapid heating of tissue, surgical smoke (also referred to as a plume, vapor, and bio-aerosols) is generated as the result of the thermal decomposition of human or animal tissue with the use of monopolar electrosurgery procedures as well as the use of lasers, ultrasonic devices and plasma energy devices. In the case of monopolar electrosurgery and lasers, the rapid heating of cells above the boiling point of their contents induces an explosive release of cellular contents as well as the pyrolysis of tissue structures. The resulting vaporization of cellular fluid releases cell contents into the surrounding air in the form of a plume of surgical smoke (see Addley, S., et. al., Surgical Smoke—What are the Risks?. The Obstetrician and Gynecologist 2019; 21:102-106).

Yet another prior art hemostatic surgery method for minimizing bleeding in human tissue, as it is being severed, is an unsharpened blade heated using a ferromagnetic coating that operates at temperatures up to 450 C for soft tissue cutting without a mechanically sharp cutting edge and up to 600 C for soft tissue ablation and vaporization. In this regard, see U.S. Pat. No. 9,220,557 (Columns 14 and 24) and FDA 510(k) Pre-Market Notification K130606 issued to Domain Surgical, Inc. In a manner similar to the monopolar electrosurgery that produces electrical arcs that can rapidly heat tissue and body fluids to temperatures above 600 C, an unsharpened blade operating at 450 C to sever tissue causes the thermal decomposition of tissue and fluids resulting in the generation and release of hazardous volatiles.

The rapid heating of tissue structures also has been observed to result in the combustion of tissue. In this regard, the auto-ignition temperature is the temperature of a substance that is the lowest temperature at which combustion occurs in normal atmosphere without an external source of ignition, such as a flame or spark. The auto-ignition temperature is required to supply the activation energy needed for combustion. For the case of the human body, the lowest auto-ignition temperature is associated with adipose tissue (i.e., fat) and is reported to be 355 C. Consequently, the temperature of any tissue of the human body heated to at least 355 C during a surgical procedure will generate volatiles (see DeHaan, J. et. al., Volatile Organic Compounds from the Combustion of Human and Animal Tissue. Science & Justice 2004; 44 [4]; 223-236).

As organic substances are heated to temperatures above 350 C, the chemical dissociation process caused by the applied thermal energy is defined as pyrolysis (see Moldoveanu, S. Pyrolysis of Organic Molecules: Application to Health and Environmental Issues. 2009; Volume 28, $1_{st}$ Edition, Elsevier Science, Amsterdam, The Netherlands). For the case of monopolar electrosurgery procedures, the region of current concentration at the tip of the active electrode causes the tissue temperature immediately adjacent to the active electrode tip to reach about 1000 C (see Palmer, J., Surgical Diathermy and Electrical Hazards: Causes and Prevention. Anesthesia and Intensive Care Medicine 2016; 17: 480-485).

For the case in which human adipose tissue is heated to 300 C, it has been observed that the amount of volatiles released is negligible based on an ion chromatogram generated using the gas chromatography/mass spectroscopy thermal desorption method to capture and analyze any substances released from human tissue samples heated to 300 C. In contrast, when human adipose tissue is heated at 500 C and 700 C, a wide range of volatiles are released based on an ion chromatogram generated using the gas chromatography/mass spectroscopy thermal desorption method. In this regard, see FIG. 6 in DeHaan, J. et. al., Volatile Organic Compounds from the Combustion of Human and Animal Tissue. Science & Justice 2004; 44 [4]; 223-236. Many of the chemicals released when human adipose tissue is heated to 500 C and 700 C are the same chemicals (i.e., hazardous volatiles) that have been identified within the smoke generated and released during monopolar electrosurgery procedures.

Chemicals identified within the smoke generated during monopolar electrosurgery procedures that are known to be potentially toxic to the operating room personnel and the patient are referred to hereinafter as "hazardous volatiles" and include the following: Acetonitrile, Acetylene, Acroloin, Acrylonitrile, Alkyl benzene, Benzaldehyde, Benzene, Benzonitrile, Butadiene, Butene, 3-Butenenitrile, Carbon Monoxide, Creosol, 1-Decene (hydrocarbon), 2,3-Dihydro indene (hydrocarbon), Ethane, Ethene, Ethylene, Ethyl benzene, Ethynyl benzene, Formaldehyde, Furfural (aldehyde), Hexadecanoic acid, Hydrogen cyanide, Indole (amine), Isobutene, Methane, 3-Methyl butenal (aldehyde), 6-Methyl indole (amine), 4-Methyl phenol, 2-Methyl propanol (aldehyde), Methyl pyrazine, Phenol, Propene, 2-Propylene nitrile, Pyridine, Pyrrole (amine), Styrene, Toluene (hydrocarbon), 1-Undecene (hydrocarbon). Xylene (see Barrett, W., et. al., Surgical Smoke—A Review of the Literature. Surgical Endoscopy 2003; 17: 979-987).

Risks of surgical smoke to operating room personnel that are generated by surgical procedures performed using monopolar electrosurgery and lasers have been reported include acute and chronic inflammatory respiratory changes (e.g., emphysema, asthma, chronic bronchitis), anemia, carcinoma, cardiovascular dysfunction, dermatitis, eye irritation, headache, hepatitis, HIV, hypoxia or dizziness, leukemia, nasopharyngeal lesions, nausea or vomiting and throat irritation. For example, upper and lower respiratory-tract symptoms associated with surgical smoke inhalation have been reported to include throat irritation, sinusitis, sneezing, asthma and bronchitis, as well as possible links to increased allergies (see Alp E. et. al., Surgical Smoke and Infection Control. Journal of Hospital Infection Control 2006; 62[1]: 1-5). In addition, xylene, toluene and ethyl benzene components associated with surgical procedures performed using monopolar electrosurgery and lasers have been reported to induce headache and eye pain (see Andreasson, S., et. al., Peritonectomy with High Voltage Electrocautery Generates High Levels of Ultrafine Smoke Particles. European Journal of Surgical Oncology 2008; 35:780-784).

Risks of surgical smoke to the patient during laparoscopic procedures involving the use of surgical procedures performed using monopolar electrosurgery occur as a result of smoke is produced inside the abdomen, since a portion of the generated smoke is absorbed through the peritoneal membrane. One of the effects in the patient's blood stream is an increase in methemoglobin and carboxyhemoglobin concentrations, thereby reducing the oxygen carrying capacity of red blood cells. An additional potential hazard for the patient is falsely elevated pulse oximeter readings, because pulse oximeter readings are compromised in the presence of dyshemoglobinemias (viz., carboxyhemoglobin and methemoglobin) that produce falsely elevated pulse oximeter oxygen readings that can result in unrecognized patient hypoxia (see Ott, D., Smoke and Particle Hazards during Laparoscopic Procedures. Surgical Service Management 1997; 3[3]: 11-13). In addition, viable contents of cancer cells can be released into the atmosphere above the surgical site as well as being into the irrigation solution during monopolar electrosurgery procedures (see Bae, M-S., et. al., Emission and Cytotoxicity of Surgical Smoke. Atmosphere 2018; 9: 381-388).

Also, intact viruses have been shown to be present within the smoke generated during monopolar electrosurgery procedures and their infectivity has been demonstrated (see Sawchuck, W., et. al., Infectious Papillomavirus in the Vapor of Warts treated with Carbon Dioxide Laser and Electrocoagulation: Detection and Protection. American Academy of Dermatology 1989; 21:41-49). In addition, the mutagenicity of smoke generated during monopolar electrosurgery procedures has been estimated to be at least that of cigarette smoke (see Tomita, Y., et. al., Mutagenicity of Smoke Condensates Induced by $CO_2$ Laser Irradiation and Electrocauterization. Mutagenicity Research 1981; 89: 145-149). It has been further shown that the smoke generated during monopolar electrosurgery procedures varies in mutagenicity depending on the type of tissue ablated. Also, the benzene smoke generated during monopolar electrosurgery procedures has been found to be principally responsible for the mutagenicity of monopolar electrosurgery smoke (see Gatti J. et. al., The Mutagenicity of Electrocautery Smoke. Plastic Reconstruction Surgery 1992; 89: 781-784).

In addition to the hazardous volatiles released during monopolar electrosurgery procedures, large quantities of cellular debris ($>1 \times 10_7$ particles/ml) were found in the plume generated by an ultrasonically energized scalpel. The concentration of cellular debris have been estimated to be about 25% of the amount of particle concentrations when compared with the plume generated by dissection of a similar amount of tissue with monopolar electrosurgery devices. Concentrations of liquid (blood or serum) aerosol were produced in a directional spray pattern when either the ultrasonically energized hook-shaped scalpel or ball-tip was used and were detected at a distance up to 40 cm from point of generation. In addition, adipose tissue was found to generate 17-23 times more particulate matter than muscle tissue. The ultrasonically energized scalpel is claimed to produce only low-temperature vapors and not "smoke" that otherwise contains hazardous chemicals. However, it is well known that lower-temperature aerosols generally increase the probability of carrying infectious and viable material than higher-temperature aerosols. It has also been experimentally confirmed that the particles released by ultrasonically energized scalpels are composed of tissue, blood and blood by-products. In this regard, see Barrett, W., et. al., Surgical Smoke-A Review of the Literature. Business Briefing: Global Surgery 2004: 1-7.

BRIEF SUMMARY OF THE INVENTION

The present disclosure is addressed to both hemostatic surgery apparatus and systems for minimizing the bleeding from tissue and transected blood vessels as are they are being severed, as well as methods of manufacture hemostatic surgical blades that overcome multiple limitations of previous manufacturing methods. Such a hemostatic surgical instrument having a surgical blade with a mechanically sharp cutting edge is referred to herein as a hemostatic surgical scalpel. The term "mechanically sharp cutting edge" of a surgical blade refers to a cutting edge that can cut tissue during a surgical procedure without the addition of any thermal, electrical and/or vibratory energy. The blade of the hemostatic surgical scalpel has a mechanically sharp cutting edge that can cut tissue in the same manner that conventional steel or stainless steel surgical blade can cut tissue. By way of example, a representative conventional surgical blade widely used in surgery and having a mechanically sharp cutting edge is the Bard-Parker Disposable Scalpel (blade size 10 or 15) available from Aspen Surgical located in Caledonia, Michigan In addition to a surgical blade having a mechanically sharp cutting edge, one or more heating elements are disposed on the blade and proximate to the mechanically sharp cutting edge of the hemostatic surgical scalpel. The one or more heating elements can be energized to controllably heat the blade to an operator selected set-point temperature. In the course of cutting tissue during a surgical procedure, the hemostatic surgical blade is controllably heated to an operator selected set-point temperature (e.g., a set-point temperature in the range from 100 C to 300 C and controlled to within ±10 C of the set point temperature). By way of example, the operator selected set-point temperature may be maintained within several Centigrade degrees of the operator selected set-point temperature under a wide range of heat dissipation levels (e.g., 5 to 40 watts) using well-known temperature feedback control or resistance feedback control methods and systems. During a surgical procedure, after energizing the one or more heating elements to increase the blade temperature to an operator selected set-point temperature, heat is transferred from the heated surgical blade to the tissue being cut, thereby limiting or stopping blood flow from severed tissue or blood vessels. During a surgical procedure and according to the teachings of the present disclosure, the maximum temperature that can be attained by any tissue or liquids within the human body that come in contact with the heated surgical blade cannot exceed the operator selected set-point temperature.

As used herein, hemostatic surgical instruments refer to apparatus, system and methods that act to stop or minimize the flow of blood from severed tissue or blood vessels within the severed tissue. During use, the hemostatic surgical blades of the present disclosure stop or minimize the flow of blood from severed tissue or blood vessels within the severed tissue by subjecting the temperature of the tissue or blood vessels to a temperature that is always below the threshold for the pyrolysis and/or thermal decomposition of tissue within the human body and the associated generation and release of hazardous volatiles from the pyrolysis and/or thermal decomposition of tissue. As used herein, pyrolysis refers to the decomposition of organic substances in a non-oxidizing atmosphere while exposed to temperatures sufficiently high to break chemical bonds. As used herein, thermal decomposition refers to decomposition of organic substances in air while exposed to temperatures sufficiently high to break chemical bonds. As used herein, tissue refers to connective tissue, i.e., the tissue that binds together and is the support for various structures of the body. The tissue is made up of fibroblasts, fibroglia, collagen fibrils and elastic fibrils and includes the collagenous, elastic, mucous, reticular and cartilaginous tissue as well as blood, lymph and interstitial fluids.

The disclosed hemostatic surgical blades are characterized by a multi-step manufacturing process to first produce a composite sheet having a symmetrical, five-layer laminar cutting portion with a cutlery-grade metal core that can be sharpened to a cutting edge which is capable of achieving a high hardness level, for instance, from 60 to 63 Rockwell C.

Preferred materials for the core of the five-layer laminate include martensitic stainless steels, high-carbon steel and titanium. By way of example of a preferred embodiment, the opposed faces of a martensitic stainless steel core are roll bonded with a highly thermally conductive metal, which advantageously may be a pure, oxygen-free high conductivity (OFHC) copper. These oppositely disposed copper layers are each bonded with an outer buttressing layer, for instance, formed of austenitic stainless steel such as a type 301 or 304. The two copper layers exhibit the same thickness and the two buttressing layers also exhibit the same thickness. Thus, the laminar blade is symmetrical and, notwithstanding, slight differences of thermal coefficients of expansion, the laminar component will not warp, for example, during the heat treatment hardening of the core or in the course of firing thick-film printed heating element layers as well as curing an outwardly disposed non-stick layer.

An extended length of this five-layer laminate (e.g., 500 feet) is next joined side-by-side in a flat plane along one edge of its length to a mating edge of a monolithic metal strip having a thickness substantially the same as the five-layer laminate to form a dual metal strip having a smooth surface at the joint between the two sides of the dual metal strip. The monolithic metal is selected from metals exhibiting a low thermal conductivity, a coefficient of thermal expansion similar to that of copper and capable of withstanding the subsequent elevated temperature of over 1,000 C required for the heat treatment of the martensitic stainless steel core that can be sharpened to a cutting edge. A preferred joining method in this regard is either electron-beam welding or laser welding and a preferred monolithic metal is stainless steel 301 or 304.

The dual metal strip provides two zones providing distinctly different thermal and mechanical properties. The first zone, comprising a five-layer laminate as described above, provides high thermal conductance as a result of the two layers of high thermal conductivity material (e.g., copper). The first zone also provides a core layer that is capable of being heat treated, hardened and subsequently sharpened as a result of the core material of heat treatable and hardenable martensitic stainless steel. The second zone provides low thermal conductance as a result of the use of a low thermal conductivity material (e.g., austenitic stainless steel 304).

The extended length of this dual metal strip comprising a first five-layer laminate zone and a second low-thermal conductivity stainless steel zone is next cut into dual metal strip lengths (e.g., about 20 inches) suitable for vertical suspension within a vacuum heat treatment furnace as required to harden the martensitic stainless steel core region of the five-layer laminate. This strip length is also suitable for subsequent computer-added cutting of blade blanks using process such a selector-discharge machining. The dual metal strip lengths are also referred to hereinafter as composite sheet strips.

Blade blanks of the required blade size are next defined in the dual metal strip lengths by cutting around approximately 99% of the perimeter of the blade blank with the cutting interrupted at one or more attachment point locations around the perimeter to form one or more supporting ligaments for retention of cut blade blanks until they are removed in preparation for the sharpening process. By way of example, a wire electro-discharge machining (EDM) process may be used for cutting the dual metal strip lengths into the required blade blank shapes.

Following the cleaning and optional grit blasting of the surface of each dual metal strip length that retains the cut blade blanks, the dual metal strip lengths and retained blade blanks are coated with a thin layer of aluminum on at least the side of the blade blanks that will subsequently be thick-film printed with one or more electrically insulative dielectric layers, one or more electrically resistive heating elements, electrically conductive leads and an electrically insulative overcoat layer. The thick-film printed electrically resistive heating element material exhibits a temperature coefficient of resistance of at least 0.0005 ohm/° C. over temperature ranges of about 20° C. to about 300° C. The thickness of the thin layer of aluminum may range from 0.0002" to 0.0020" and may, by way of example, be deposited by ion vapor deposition, physical vapor deposition, plasma spraying or electroplating. An aluminum layer is deposited on the blade surface to enable chemical reaction bonding to thick-film printable dielectric inks formulated for reaction bonding to aluminum substrates. By way of example, thick-film printable dielectric inks are commercially available that have been formulated for thick-film printing and firing on aluminum heat sinks used in the manufacture of most light emitting diode (LED) light sources. However, the melting point of aluminum is only about 650 C while the minimum heat treatment temperature required for hardening the martensitic steel core that can be sharpened to a cutting edge is about 1000 C. Hence, a novel manufacturing process also is the subject of this invention in which the efficient deposition of the aluminum coating occurs after the hardening of the martensitic steel core material within the blade laminate.

Following the deposition of a thin layer of aluminum on one side of each dual metal strip length (i.e., composite sheet length) that retains the cut blade blanks, each previously cut blade blank is separated from the dual metal strip by breaking or cutting the one or more ligaments that support each blade blank. In a preferred embodiment, that portion of the individual blade blank perimeter intended for incising tissue is next sharpened using a sequence of processes that may include, by way of example, a first step involving mechanical grinding of the blade blanks resulting in a cutting edge region having a double facet with a preferred included angle of about 22 degrees. The mechanical grinding may be performed using an abrasive grinding wheel followed by a second step involving stropping the edge using a leather and/or cotton wheel to remove any burrs or metallic residues formed during the first mechanical grinding step. In a preferred third step, or in place of the aforementioned second stropping step, an electrochemical honing or deburring (i.e., sharpening) process may be used as the final step in the sharpening of each blade blank. Alternatively, the first step in blade sharpening may employ an electrochemical process wherein an electric current flows between a negatively charged abrasive wheel and the positively charged blade blank through an electrolyte (e.g., sodium chloride) solution. A chemical reaction action occurs forming an oxidized surface on the blade blank surface being sharpened. The oxidized surface is removed by the specially formulated abrasives in the wheel, thereby exposing more material and repeating the cycle to form a sharp, burr-free cutting edge.

The sharpened blades are next cleaned, dried and heated in an oven to remove any residual liquid water and/or solvent agents. The blades are next placed onto plates having machined cavities on their top surface (hereinafter to referred to as "setters") that match the outline of the sharpened blades and that prevent any direct contact between the sharpened blades and the setter to avoid any unwanted dulling of the sharpened blade edge. Alternatively, the cleaning and drying steps may be performed after sharpened blades have been placed in the setters. The position of the machined cavities on the on the top surface of the setters are accurately positioned to align with the thick-film printing screens used to screen-print multiple layers of dielectric, resistor and conductor thick-film inks.

In a preferred embodiment, a first electrically insulative dielectric thick-film ink layer is printed over most of the lateral surface area of the sharpened blade on the side of the sharpened blade coated with a thin layer of aluminum. Following printing, this first layer of dielectric thick-film ink is fired in an air oven (e.g., at 510 C).

Next, while the sharpened blades are still located within the cavities of the setter, one or more electrically insulative dielectric thick-film ink layers are printed over the fired first layer of dielectric in order to minimize the possibility of any small sites (i.e., commonly referred to as "pin-holes") that may not have been fully covered with the first layer of dielectric ink. Following printing, these one or more additional layers of dielectric thick-film ink are fired after each printing in an air oven (e.g., at 510 C).

Next, while the sharpened blades are still located within the cavities of the setter, a third layer comprising an electrically conductive thick-film ink is next printed over the previously fired dielectric layers to form a low electrical resistance lead pattern on that portion of sharpened blade comprised of the low thermal conductivity stainless steel that extends from the vicinity of and distal to the weld zone to the proximal end of the sharpened blade. Following printing, this third layer of an electrically conductive thick-film ink is fired in an air oven, preferably at a temperature lower (e.g., at a temperature of 450 C) than the firing temperature employed for the dielectric layers to prevent migration of the electrically conductive thick-film ink layers through the electrically insulative dielectric layers.

Next, while the sharpened blades are still located within the cavities of the setter, a fourth layer comprising an electrically resistive thick-film ink is next printed over the previously fired dielectric layers to form one or more electrically resistive heating elements (e.g., one or more serpentine resistive heater configurations) on that portion of the sharpened blade comprised of the thermally conductive five-layer laminate. The proximal terminations of the electrically resistive heating elements are positioned so that they overlap corresponding terminations at the distal end of the electrical leads to provide electrical communication between the electrical leads and the one or more electrical heater segments. Following printing, this fourth layer of an electrically resistive thick-film ink is fired in an air oven, preferably at a temperature lower (e.g., at a temperature of 450 C) than the firing temperature employed for the dielectric layers to prevent migration of the electrically resistive thick-film ink layers through the electrically insulative dielectric layers.

A fifth thick-film printing and firing step, while the sharpened blades are still located within the cavities of the setter, an electrically insulative dielectric thick-film ink overcoat layer is printed over the previously printed and fired lead pattern and heater pattern except in the proximal portion of the lead pattern intended to electrically communicate with corresponding electrical contacts within the handle. Following printing, this fifth layer of an electrically insulative thick-film ink is fired in an air oven, preferably at a temperature lower (e.g., at a temperature of 450 C) than the firing temperature employed for the original electrically insulative dielectric layers to prevent migration of the previously printed electrically conductive and electrically resistive thick-film ink layers through the adjacent electrically insulative dielectric layers.

Following the thick-film printing and firing process steps described in the preceding paragraphs, the sharpened blades with one or more deposited resistance heaters and leads and electrically insulative overcoat are next coated with a non-stick coating in those distal portions of the blade that can come in contact with tissue during use in surgery. The portions of the sharpened blade on which a non-stick coating is deposited exclude the proximal portion of the lead pattern intended to electrically communicate with corresponding electrical contacts within the handle. The thickness of the deposited non-stick coating is sufficiently thin to eliminate the need for wiping of the portion of the blade facets that are within about 0.005 inch of the tip of the cutting edge of the blade as previously required for non-stick coatings having a deposited thickness in the range from 0.0005 to 0.0010 inch. By way of example, the non-stick coating may be deposited on the tissue-contacting surfaces of the sharpened blade using a spraying process. After the deposition process, the non-stick coated blade is heated in an air oven at an elevated temperature (e.g., 330 C) for a short period (e.g., 15 minutes) during which the non-stick coating is dried and adhered to the blade surface. In a preferred embodiment, the thickness of the adhered non-stick coating is in the range from about 0.00005 inch to 0.00010 inch. The preferred non-stick coating thickness in the range from 0.00005 inch to 0.00010 inch corresponds to a preferred thermal resistance in the range from 0.05 to 0.10 C/watt-$cm_2$ associated with heat conducted from the facets of sharpened blade to the contacted tissue. An even more preferred non-stick coating thickness is not greater than 0.00005 inch. Even at the low level of thermal conductivity of the preferred non-stick coating, a non-stick coating thickness as small as 0.00005 to 0.00010 inch results in a temperature difference between the heated surgical blade supporting the non-stick coating and the surface of the non-stick coating in contact with tissue of only 4 to 8 C, respectively, at a typical heat dissipation level of 25 watts and tissue contact surface area.

Following the application of a non-stick coating to the tissue-contacting surfaces of the sharpened blade, the proximal portion of the sharpened blade that does not contact tissue during surgical use may optionally be mechanically and/or adhesively attached to a thermally insulative sleeve (e.g., injection molded plastic sleeve) that enables [a] grasping the proximal portion of the sharpened blade for the purposeful step of insertion or removal of the sharpened blades from the handle while [b] avoiding physical contact with the sharpened cutting edge and/or the heated portion of the blade during the blade insertion or removal step.

Next, the electrical resistance of each of the one or more electrically resistive heating elements is measured at room temperature to determine if their electrical resistance is within a predetermined range (e.g., 5.0±0.5 ohms). If the electrical resistance of each of the one or more electrically resistive heating elements is within a predetermined range, then the sharpened blade may be inserted into a handle and power applied to the one or more electrically resistive heating elements to rapidly raise the temperature of the one or more electrically resistive heating elements to an elevated temperature (e.g., raise heater temperature to 300 C within 3 seconds) to simulate the heating up transients associated with actual use of blades during surgical procedures.

Finally, each non-stick coated, sharpened blade that satisfies quality assurance tests, as exemplified in the preceding paragraph, is placed in and hermetically sealed within a package or pouch. The non-stick coated, sharpened blade contained within a sealed package or pouch is exposed to well established medical device sterilization procedures. A multiplicity of packaged blades may be placed within a carton containing, by way of example, 10 individually packaged blades. Multiple cartons may be placed in a larger box for subsequent sterilization. By way of example, sterilization of the non-stick coated surgical blades may be performed on cartons or boxes of surgical blades using either [a] gamma radiation emitting isotopes such as Cobalt 60 or Cesium 137 or [b] ethylene oxide gas sterilizing agents.

Further disclosed is a method for manufacturing a hemostatic surgical blade having a laminar portion structure and a stem portion structure, providing improved sharpness during surgical procedures as well as improved conduction of heat into tissue being incised thereby providing an improved level of hemostasis while transecting blood vessels within tissue. The disclosed method for manufacturing a hemostatic surgical blade comprises the steps:

- providing a core strip of cutlery grade steel, preferably martensitic stainless steel, having a widthwise extent effective for forming the laminar portion and a thickness defined between oppositely disposed faces of the core strip;
- providing layers (116, 118) of a metal exhibiting high thermal conductivity, having a conduction thickness and shape for bonding against each face of the core strip;
- providing two buttressing strips of austenitic stainless steel having a shape corresponding with the shape of the layers (116, 118) of a metal exhibiting high thermal conductivity;
- roll bonding the thermal transfer strip with a face of the core strip and a buttressing strip with each thermal transfer strip to provide a symmetrical, five-layer laminar strip having a lamination thickness;
- providing a stem strip of metal exhibiting low thermal conductivity having a thickness corresponding with the lamination thickness and shape effective to form stem portion structure;
- edge welding the stem strip to the laminar strip to provide a composite sheet;
- heat treating the composite sheet to an extent effective to harden the martensitic stainless steel;
- cut blade blanks within the composite sheet while maintaining one or more small attachments between the blade blanks and the composite sheet;
- depositing a layer of aluminum on the surface of one side of the blade blanks after they have been cut and while still partially attached to the composite sheet;
- removing the aluminum coated blade blanks from the composite sheet and sharpening the martensitic stainless steel core and adjacent laminate layers of blanks to define a scalpel edge having a double facet;
- depositing successive thick-film printed and fired layers including electrically insulative dielectric layer, one or more electrically resistive heating elements, electrically conductive leads and electrically insulative overcoat layer; and
- depositing a very thin non-stick coating over those portions of the heatable surgical blade that may contact tissue during surgical use.

In addition, further disclosed is a hemostatic surgery apparatus, system and method for minimizing the bleeding from tissue, including transected blood vessels, as they are being severed using a heated surgical blade whose maximum operating temperature, also referred herein as the operator selected set-point temperature, is below the threshold for pyrolysis and/or thermal decomposition of human tissue with the associated release of hazardous volatiles. By way example, the hazardous volatiles generated and released as a result of pyrolysis and/or thermal decomposition of the heated tissue as it is severed or treated include volatiles in the form of smoke, particulate matter and bio-aerosols comprising a range of chemical species. The hazardous volatiles known to be released during the use of monopolar electrosurgery and laser surgical devices are avoided by limiting the maximum operator selectable set-point temperature of the heated surgical blade of the present disclosure to an upper limit of 300 C also referred to as a maximum set point temperature of 300 C. An upper limit surgical blade temperature of 300 C is known, through multiple published studies, to be below the threshold for the pyrolysis and/or thermal decomposition of human tissue (including blood and other fluids within the body) and the associated generation of hazardous volatiles. At a maximum heated surgical blade temperature of 300 C, the only volatile that can be released from transected and treated tissue is benign water vapor (i.e., steam) as a result of the evaporation of the water component within the cells that comprise the tissue being transected. Limiting the maximum temperature of the heated surgical blade of the present disclosure to not greater than 300 C assures that no tissue structures during a surgical procedure can be heated to a temperature above 300 C since the heating of tissue in contact with the heated surgical blade is heated only through the process of conduction and radiation heat transfer from the heated surgical blade to the adjacent tissue being transected or treated. Furthermore, unavoidable thermal resistances in the conduction and radiation heat transfer pathway between the temperature controlled electrically resistive heating element (e.g., a heating element operating at a maximum operator selected temperature of 300 C) and the contacted tissue and the adjacent tissue being transected or treated assure that the maximum tissue temperature can not exceed the maximum operator selectable set-point temperature of the hemostatic surgical blade under any surgical conditions.

The avoidance of the release of hazardous volatiles during the use of the hemostatic surgery apparatus, system and method of the present disclosure significantly reduces the health risks to the operating room personnel as well as the surgical patient associated with the use of monopolar electrosurgery procedures and laser surgical devices. In addition, unlike high-frequency ultrasonic surgical instruments that can disperse particular matter into the air surrounding the surgical site, the non-vibrating hemostatic surgery apparatus, system and method of the present disclosure avoids the generation and release of cellular debris including particles composed of tissue, blood and blood by-products.

Other objects of the disclosure will, in part, be obvious and will, in part, appear hereinafter.

The disclosure, accordingly, comprises the apparatus, method and system possessing the construction, combination of elements, arrangement of parts and steps, which are exemplified in the following detailed description.

BRIEF DESCRIPTION OF THE SEVERAL VIEWS OF THE DRAWINGS

For a fuller understanding of the nature and objects hereof, reference should be made to the following detailed description taken in connection with the accompanying drawings.

FIG. 4A is a sectional view taken through line of 4A-4A of FIG. 4 showing five-layer laminate region of sharpened blade substrate on which is disposed an aluminum layer;

FIG. 6 is a sectional view taken through line of 6-6 of FIG. 5 showing five-layer laminate region of sharpened blade substrate on which is successively disposed an aluminum layer followed by an electrically insulative dielectric layer, an electrically resistive heating element layer, an electrically insulative dielectric overcoat layer and a non-stick coating layer on the outer surface of the blade assembly;

FIGS. 8A-8D combine as labeled thereon to provide a flow chart describing the manufacture of surgical blades as at FIGS. 2 through 7.

The drawings will be described in further detail below.

DETAILED DESCRIPTION OF THE INVENTION

In the disclosure to follow, initially described is a surgical blade 12 for a hemostatic surgical instrument 10, preferably incorporating a martensitic stainless steel core which is surmounted by thermal transfer layers formed of copper which, in turn, are supported by austenitic stainless steel buttressing layers to provide a symmetrically disposed five-layer laminate blade. Alternatively, the core of the five-layer laminate may be a material capable of being sharpened to mechanically sharp cutting edge such as high-carbon steels, tempered steels and titanium alloys. Edge welded to the five-layer laminate blade region is a solid stem material portion formed of a metal exhibiting a low thermal conductivity such as an austenitic stainless steel to form a composite sheet having a weld line separating the five-layer laminate blade region is a solid stem material portion. Blade profile shapes are cut from the laminate sheet to form blade blanks. Prior to separating the cut blade blanks from the composite sheet, an aluminum layer is deposited onto the side surface of the composite sheet retaining cut blade blanks, the deposition being on the same side as the side to receive subsequent thick-film printed and fired electrically insulative dielectric layers, electrically resistive heating element layer, electrically conductive lead layer and overcoat layer. The laminate portion is heated by one or more electrically resistive heating elements deposited on an intermediate electrically insulative dielectric layer that has been previously deposited on the five-layer laminate blade. Electrically conductive leads are deposited on the stem portion structure and are in electrical communication with the electrically resistive heating element terminals located distal to the weld line in the five-layer laminate blade portion.

The disclosure that follows specifies improved manufacturing techniques employed for the preferred embodiment that provide increased blade sharpness and increased level of hemostasis while incising blood vessels within tissue.

Figure 1:
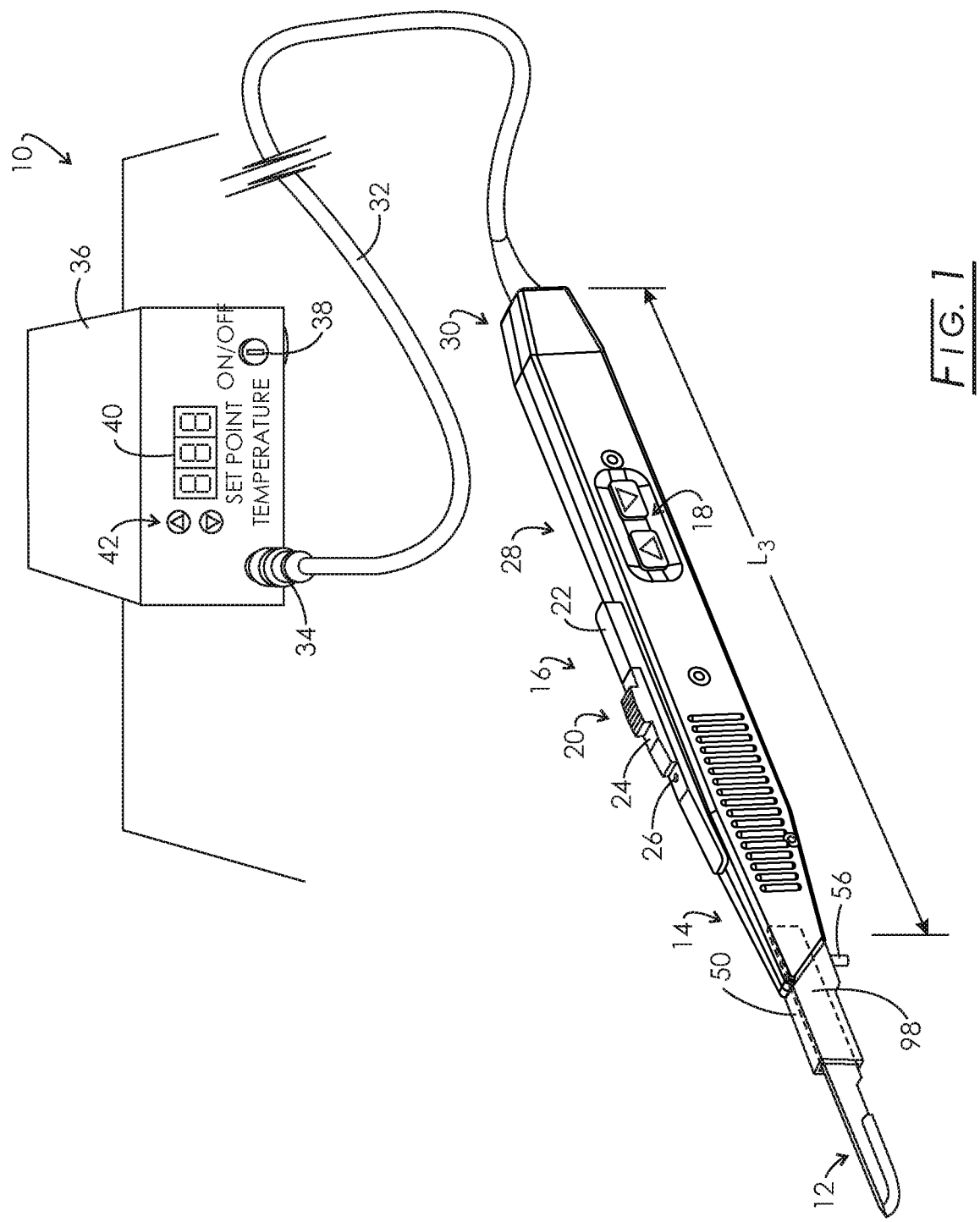
FIG. 1 is a pictorial representation of a hemostatic surgical instrument system.

Referring to FIG. 1, the system of the invention is represented in general at 10. System 10 includes a hemostatic surgical blade represented generally at 12, the stem portion structure of which has been mounted within the forwardly disposed engagement portion 14 of a scalpel handle represented generally at 16. Handle 16 is seen to support a temperature level adjusting up/down switch assembly represented generally at 18 and a cantilever-type operating switch represented generally at 20. The up/down switch assembly represented generally at 18 enables the operator to select a set-point temperature for the surgical blade 12 during use that is within the range from about 100 C to a maximum temperature that is below the generation of hazardous volatiles, i.e., a maximum temperature not exceeding 300 C. Switch 20 includes two hand actuateable components, a coagulation switch component 22 which when depressed causes the surgical blade 12 to accelerate in temperature to the highest allowable set-point temperature of 300 C. Forwardly of component 22 is a sliding switch component 24 shown in its closed or operating orientation such that surgical blade 12 will be heated to that temperature elected, for example, utilizing the up/down switch assemblage 18. A small red dot 26 is revealed in this orientation to apprise the surgeon that the blade is receiving electrical energy. Sliding switch component 24 forwardly turns off the delivery of energy to surgical blade 12 and covers red dot 26.

Still referring to FIG. 1, a handle control circuit (not shown) within the handle 16 extends to a terminal assembly (not shown) located at the rearward end 28 of handle 16. That terminal assembly engages a cable connector assembly within handle 16 and represented generally at 30. The ten or more electrical leads associated with the connector assembly 30 then extend via cable 32 to a console connector 34 that is seen to be removably engaged within an appropriate receiving connector within the console 36 of a controller. Controller functions within the console 36 include an on/off switch 38, a surgical blade set-point temperature readout 40 and a temperature up/down switch assemblage represented generally at 42. Assemblage 42 carries out the same function as assemblage 18 on the handle 16. As before, the up/down switch assemblage represented generally at 42 enables the operator to select a set-point temperature for the surgical blade 12 during use that is within the range from about 100 C to a maximum temperature that is below the threshold for the generation and release of hazardous volatiles, preferably a maximum allowable heated surgical blade temperature not exceeding 350 C and more preferably a maximum allowable heated surgical blade temperature not exceeding 300 C. The maximum allowable heated surgical blade temperature is determined by the maximum allowable operator selectable set-point temperature using up/down switch assemblage 42. By way of example in a preferred embodiment, the maximum allowable surgical blade temperature is to 300 C by limiting the maximum allowable operator selectable set-point temperature to 300 C.

Hazardous volatiles that are known to be generated and released during the use of monopolar electrosurgery and laser surgical devices are thereby avoided by limiting the maximum temperature of the heated surgical blade 12 of the present disclosure to an upper limit of 300 C, an upper limit temperature that is known, through multiple published studies, to be below the threshold for the generation of hazardous volatiles. At a maximum heated surgical blade temperature of 300 C, the only volatile that can be released from transected and treated tissue is benign water vapor (i.e., steam) as a result of the evaporation of the water component within the cells that comprise the tissue being transected.

Returning to engagement portion 14 and surgical blade 12, while the stem portion structure 98 of surgical blade 12 is retained mechanically and/or magnetically and is associated electrically with the control circuit of handle 16, it also is seen being associated with a thermally insulative sleeve represented generally at 50 which functions as a means for grasping surgical blade 12 during insertion or removal of surgical blade 12 while minimizing the risk of injury caused by mechanically sharp cutting edge and/or thermal injury due to residual heat within surgical blade 12 following use at high temperatures (e.g., the maximum operator selectable temperature of 300 C for surgical blade 12). By way of example, thermally insulative sleeve may be injection molded using a plastic with a high continuous use temperature of over 170 C such as polyetherimide (e.g., Ultem) available from Technical Products, Inc., Hubertus, Wisconsin). The sleeve 50 is retained in position by a registration detent formed within the stem portion structure 98 of surgical blade 12.

Figure 2:
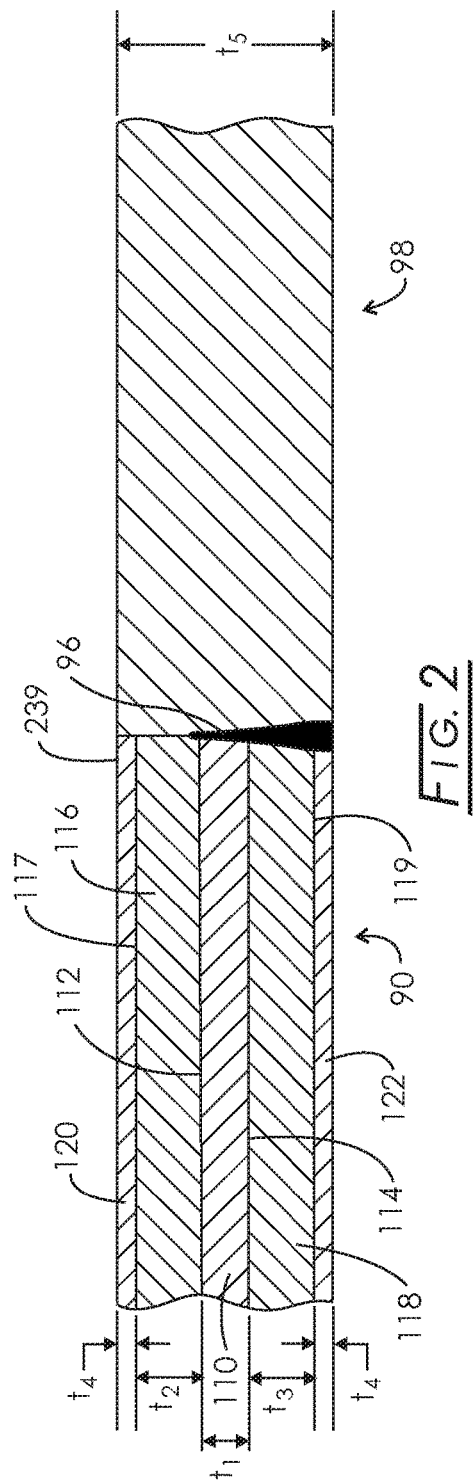
FIG. 2 is a sectional view taken through the five-layer laminate strip and adjoining low thermal conductivity solid stem material in the vicinity of the weld line taken through line 2-2 in FIG. 3.

Looking to FIG. 2, a partial sectional view generally taken across the weld 96 shows laminar cutting portion structure 90 as well as stem portion structure 98. The laminar cutting portion structure 90 is joined to the stem portion structure 98 at weld 96 formed at their interface. By way of example, weld 96 can be formed by a electron-beam welding process or a laser welding process.

Still referring to FIG. 2, laminar cutting portion structure 90 is seen to be configured having a core 110 which is formed of a martensitic stainless steel with a thickness in the range from about 0.005 inch to about 0.010 inch, and preferably 0.007 inch. In general, stainless steels are iron-based alloys containing a minimum of about 10.5% chromium that forms a protective, self-protective oxide film giving them corrosion resistance. Other alloying elements are added to the steels to develop desired characteristics. In this regard, martensitic stainless steels, while being based on the addition of chromium as the major alloy element, exhibit higher carbon and generally lower chromium content. Core 110 preferably is formed with an AISI type 440C, 420C stainless steel, Hitachi Metal's stainless steel having the trade name GIN-4 or GIN-5 or Sandvik Materials Technology's stainless steel having the trade name Sandvik 13C26. The oppositely disposed faces of core 110 are seen at 112 and 114. Roll bonded to each of these faces 112 and 114 is a respective thermal transfer layer as at 116 and 118. Advantageously, layers 116 and 118 are provided as being formed of a pure, oxygen-free high conductivity (OFHC) copper having a thickness in the range from about 0.010 inch to about 0.020 inch, and preferably 0.014 inch. To assure the stiffness of layers 116 and 118, they are roll bonded with a stainless steel buttressing layer as represented respectively at 120 and 122. By way of example, stainless steel layers 120 and 122 may be formed of an austenitic stainless steel. This group of stainless steels contains at least 16% to 20% chromium and 6% to 10% nickel corresponding to stainless steel types 301 and 304. Alternatively, layers 120 and 122 may be formed of a precipitation hardened stainless steel, for example, type 17-7PH or 17-5PH. The layers 120 and 122 will exhibit a thickness of between about 0.002 inch and 0.004 inch.

It is important to observe in FIG. 2 that the metal laminate structure at laminar cutting portion structure 90 is symmetrical. In this regard, the core 110 is surmounted by layers 116 and 118 having a high thermal conductivity and having equal thickness that are, in turn, surmounted and buttressed by stainless steel layers 120 and 122 at outwardly disposed surfaces 117 and 119 of layers 116 and 118, respectively. The stainless steel layers 120 and 122 are additionally of equal thickness. The overall thickness of the laminar cutting portion structure 90, $t_5$ following roll bonding is preferably in the range from 0.027 to 063 inch. Accordingly, notwithstanding that the layers may exhibit slightly different thermal expansion coefficients the symmetry of the five-layer laminate serves to avoid warpage because of differential expansion.

Looking to stem portion structure 98, note that its thickness corresponds with that of laminar cutting portion structure 90. Stem portion structure 98 may, for example, be formed of an austenitic stainless steel type 304 that exhibits a low thermal conductivity to limit the amount of heat that is conducted from the laminar cutting portion structure 90 to the handle 16 during surgical use when surgical blade 12 is operating at an elevated temperature, the stem portion structure 98 being supported by handle 16 as seen in phantom view shown in FIG. 1

Figure 3:
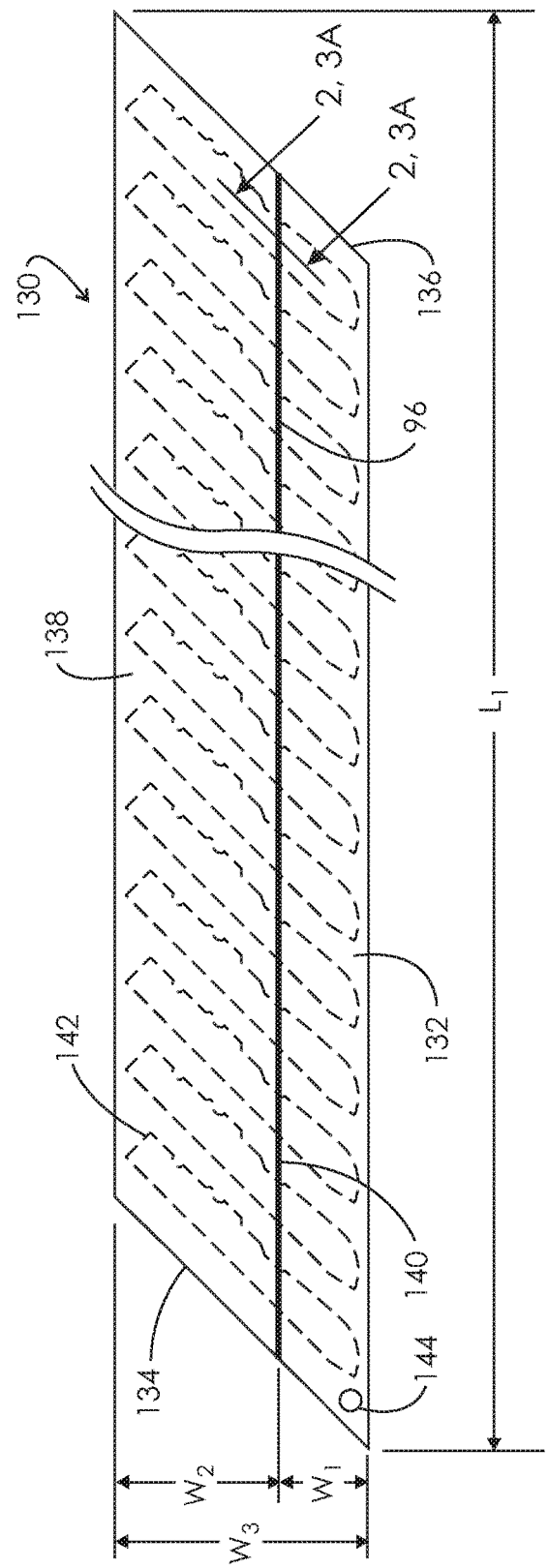
FIG. 3 is a top view of a composite sheet formed of laminar material and solid stem material as is developed during the fabrication of hemostatic surgical blade blanks wherein the blade blanks remain attached to composite sheet until after deposition of aluminum layer.

Turning to FIG. 3, a composite sheet (also referred to hereinafter as a "dual metal laminate") represented generally at 130 is illustrated in top view fashion. Composite sheet 130 is shown with a slanted quadrilateral periphery, the slant representing an angle of about 45°. Prior to cutting composite sheet 130 to a nominal length of about 20 inches to facilitate subsequent electro-discharge machining, the composite sheet 130 is formed by joining an extended length of first strip 132 (e.g., 500 feet) of laminar cutting portion structure 90, trimmed to a desired width W1, to an equal length of second strip 138 of stem portion structure 98, trimmed to a desired width W2, along weld line 140. The first strip 132 of laminar cutting portion structure 90 is edge welded to second strip 138 of stem portion structure 98 which is formed, for example, of austenitic stainless steel of type 304 as disclosed at stem portion structure 98 in FIG. 2. Such edge welding of the two strips is preferably performed in long lengths (e.g., 500 feet) prior to cutting the dual metal assemblage into shorter strip lengths as seen in FIG. 3. The edge weld line between strips 132 and 138 is shown at 140.

Following cutting the composite sheet 130 into shorter lengths as seen in FIG. 3 and to permit the composite sheet 130 to be held in a vertical orientation while being heat treated to increase the hardness of core 110, a hole 144 is drilled at the upper edge region of second strip 138. Thus, warpage can be avoided during this heat treatment step in the production process. The heat treating process may be performed in a vacuum furnace or a furnace back-filled with a non-oxidizing atmosphere (e.g., nitrogen) or a reducing atmosphere (e.g., hydrogen) since the heat treatment of the core 110 to achieve the high level of hardness needed for the sharpening and durability of the scalpel cutting edge requires temperatures of about 1000° C. or greater.

Following heat treatment of the composite sheet 130 seen in FIG. 3, blade blanks are cut as shown in phantom extending across these sheets, certain of blade blanks being identified at 142. The cutting of these blade blanks may be performed by electro-discharge machining with a multiplicity of composite sheets 130 arranged in a stack of composite sheets 130 (e.g., 40 strips per stack). The cutting of the composite sheets 130 to form blade blanks 142 is continued over most of the perimeter of blade blanks 142 while leaving a small ligament (e.g., uncut length of 0.040 inch) so that the blade blanks 142 remain attached to composite sheets 130 during the subsequent deposition of aluminum on at least one side of composite sheet 130 as seen in FIG. 3.

Figure 3A:
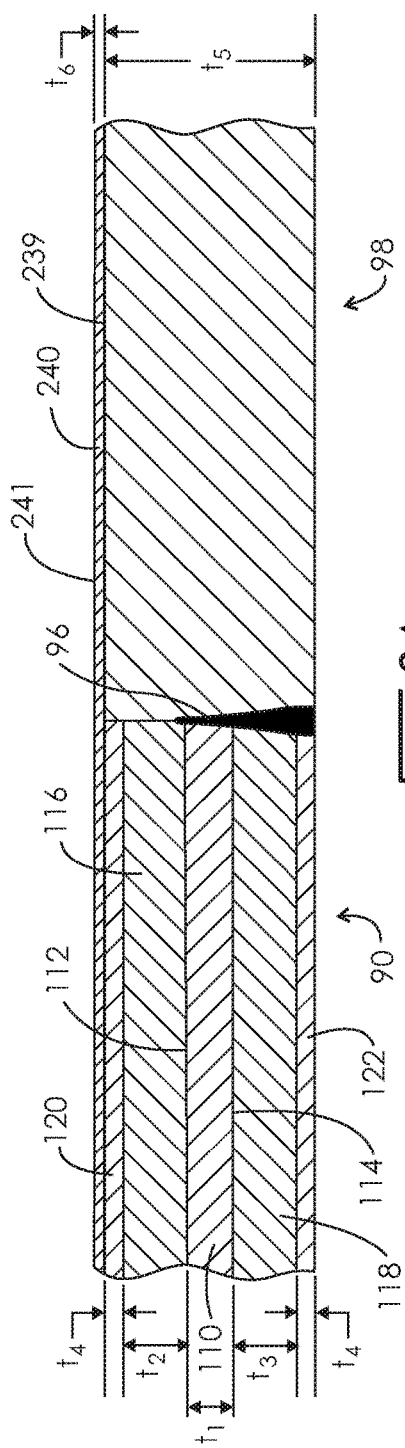
FIG. 3A is a sectional view taken through the five-layer laminate strip and adjoining low thermal conductivity solid stem material in the vicinity of the weld line after the deposition of an aluminum layer and taken through line 3A-3A in FIG. 3.
Figure 3B:
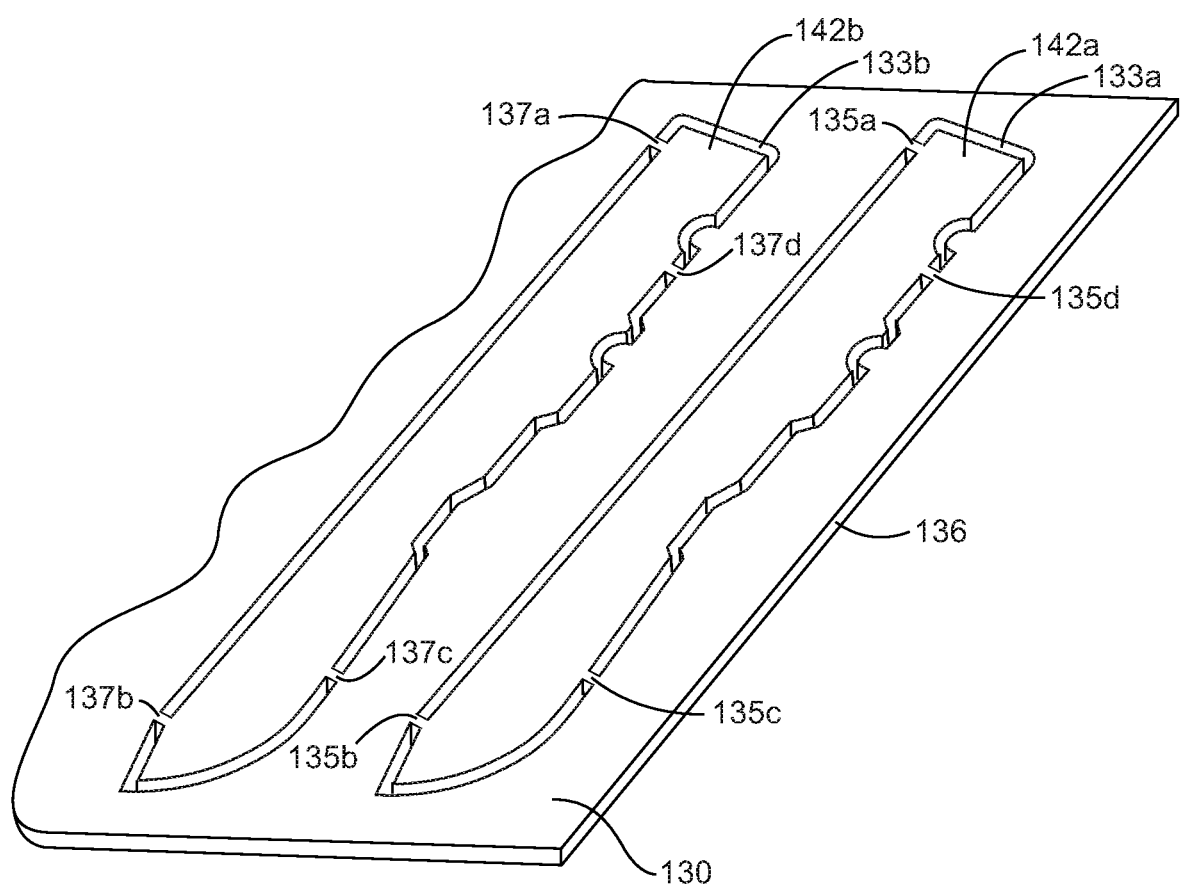
FIG. 3B is an isometric view of the composite sheet showing cutting of the blade blanks.

A partial view of a composite sheet 130 is seen in isometric view in FIG. 3B following the cutting of blade blanks 142a and 142b. By way of example, as seen in FIG. 3B, the entire perimeter of blade blank 142a is cut using electro-discharge machining (EDM) within composite sheet 130 forming perimeter gap 133a except for four ligaments 135a-135d. A greater or less number of ligaments may be used. Ligaments 135a-135d may, for example, each have a width and length of 0.040 inch and blade blank 142a remains attached to composite sheet 130 until after the subsequent deposition of aluminum layer 240 as seen in FIG. 3A. Likewise, as seen in FIG. 3B, the entire perimeter of blade blank 142b is cut using electro-discharge machining within composite sheet 130 forming perimeter gap 133b except for four ligaments 137a-137d. The ligaments 137a-137d may, for example, each have a width and length of 0.040 inch and blade blank 142b remains attached to composite sheet 130 until after the subsequent deposition of aluminum layer 240 as seen in FIG. 3A.

Following the cutting of composite sheet 130 into defined blade blanks 142 that remain attached to composite sheet 130, each composite sheet is cleaned and optionally grit blasted to prepare at least one of the side surfaces for aluminum deposition. The side surface of composite sheet 130 on which an aluminum layer is deposited is the same side surface upon which an insulative dielectric layer, one or more electrically resistive heating elements, electrically conductive leads and electrically insulative overcoat layer are sequentially thick-film printed and fired. Importantly, the deposition of the aluminum layer 240 onto blade surface 239, as seen in FIG. 2, is accomplished while the defined blade blanks 142 remain attached to composite sheet 130 to facilitate the aluminum deposition process steps.

Looking now to FIG. 3A, a partial sectional view generally taken across the weld 96 shows laminar cutting portion structure 90 as well as stem portion structure 98 as seen in FIG. 2 with the addition of an aluminum layer 240 deposited on at least one side surface of the composite sheet 130 seen in FIG. 3. Preferably, a thin layer of pure aluminum ranging in thickness from 0.0002 inch to 0.002 inch is deposited on the surface the blade blanks upon which an insulative dielectric layer, one or more electrically resistive heating elements, electrically conductive leads and electrically insulative overcoat layer are sequentially thick-film printed and fired. The aluminum layer 240 provides a chemical reaction with and secure bonding to commercially available, electrically insulative dielectric thick film inks such as DuPont AS-100 available from DuPont Microcircuit Materials (Research Triangle Park, North Carolina) or Celcion IP6080 available from Heraeus Electronics (Hanau, Germany). By way of example, the aluminum layer 240 seen in FIG. 3A may be deposited by ion vapor deposition (e.g., Titanium Finishing Company located in East Greenville, Pennsylvania).

Following the deposition of aluminum layer 240 on composite sheet 130, the individual blade blanks 142 are separated from composite strip 130 by breaking or cutting the small ligaments that heretofore retained the blade blanks 142 within the composite strip 130.

Figure 4:
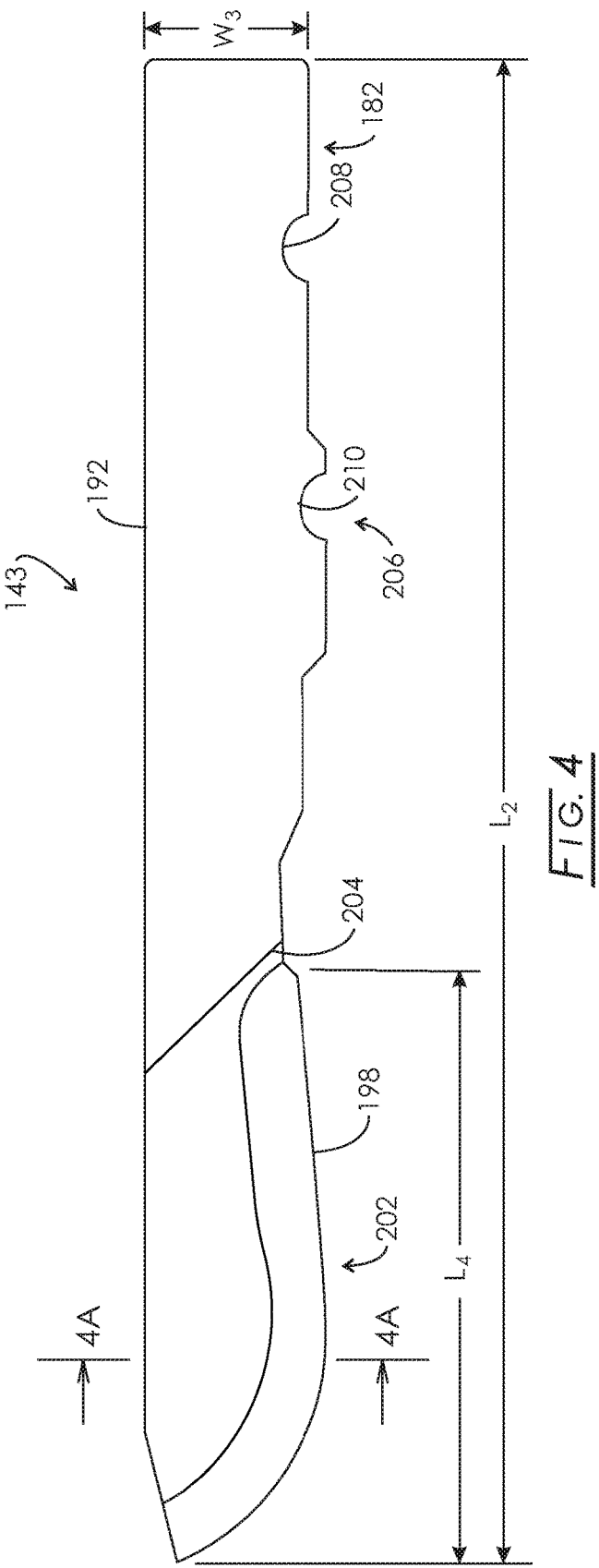
FIG. 4 is a side view of one of the hemostatic surgical blade blanks of FIG. 3 after aluminum deposition and sharpening.

Referring now to FIGS. 3A, 4 and 4A, individual blade blank 142 is next sharpened by mechanical grinding and honing (e.g., electrochemical honing) to define sharpened blade substrates 143 having cutting edge region 202 of laminar cutting portion structure 90 with mechanically sharp cutting edge 198. In a preferred embodiment, that portion of the individual blade blank perimeter intended for incising tissue is sharpened using a sequence of processes that may include, by way of example, a first step involving mechanical grinding of blade blanks 142 resulting in a cutting edge region 202 having a double facet with a preferred included angle, $\Phi$ of about 22 degrees. As seen in FIG. 4A, cutting edge region 202 includes first facet 250 and second facet 252. The mechanical grinding may be performed using an abrasive grinding wheel followed by a second step involving stropping the edge using a leather and/or cotton wheel to remove any burrs or metallic residues formed during the first mechanical grinding step. In a preferred third step, or in place of the aforementioned second stropping step, an electrochemical sharpening process (also referred to as electrochemical honing or electrochemical deburring process) may be used as the final step in the sharpening of each blade blank 142. Alternatively, the first step in blade sharpening may employ an electrochemical sharpening process wherein an electric current flows between a negatively charged abrasive wheel and the positively charged blade blank 142 through an electrolyte (e.g., sodium chloride) solution. A chemical reaction action occurs forming an oxidized surface on the surface of the blade blank 142 being sharpened. The oxidized surface is removed by the specially formulated abrasives in the wheel, thereby exposing more material and repeating the cycle to form a sharp, burr-free cutting edge 198.

Next, referring to FIG. 4, a multiplicity of sharpened blade substrates 143 are accurately positioned within a thick-film printing fixture or setter (not shown) utilizing registration detents 208 and 210 in combination with upper edge 192 of sharpened blade substrate 143. Each sharpened blade substrate 143 is accurately and securely positioned within the machined cavities on the on the top surface of the setters so that cutting edge 198 do not physically contact the setter, thereby maintaining the sharpness of the cutting edge 198. The position of the machined cavities on the on the top surface of the setters are accurately positioned to align with the thick-film printing screens used to screen print multiple layers of dielectric, resistor and conductor thick-film inks. Following solvent cleaning of the upper surface of sharpened blade substrates 143 while positioned within the setter, the setter and sharpened blade substrates 143 are placed in an oven to remove any liquid residue dry in an air oven at about 400 C.

Following cleaning and drying of the upper surface of each sharpened blade substrate 143 as seen in FIG. 4, a blade heating circuit 249 is disposed on surface 241 of aluminum layer 240 through a succession of thick-film printing and firing steps that are sequentially performed to deposit one or more electrically insulative dielectric layers 242, electrically conductive leads 176-179, an electrically resistive heating element layer 244 to form one or more electrically resistive heating elements 171 and an electrically insulative dielectric overcoat layer 246. The thick-film printing and firing of each of these successive layers is described in greater detail below in connection with FIGS. 5, 6 and 7.

Figure 5:
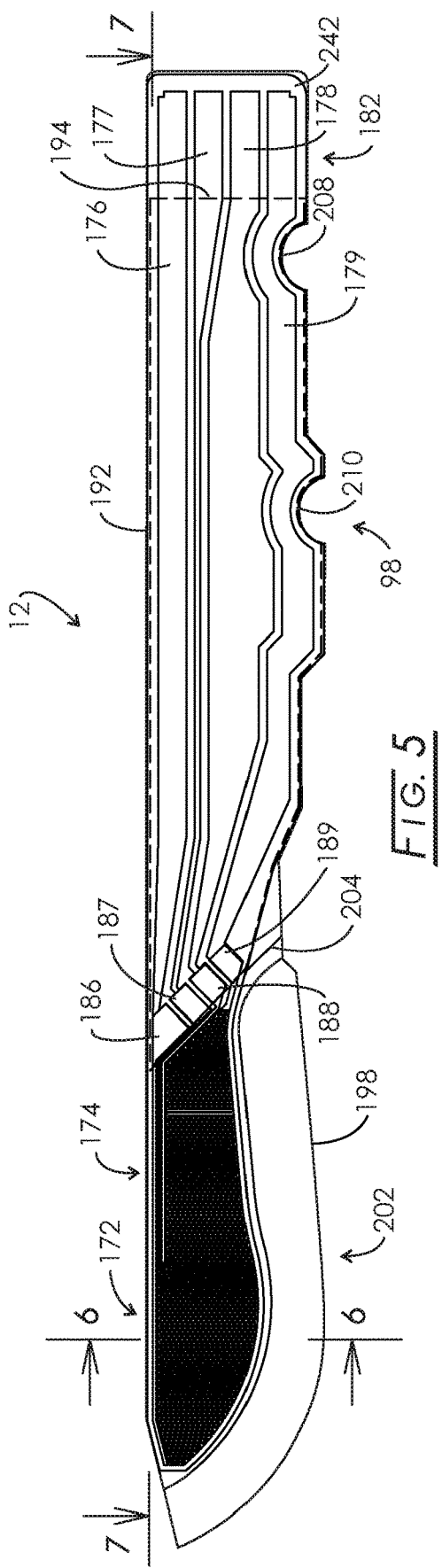
FIG. 5 is a side view of one of the hemostatic surgical blade blanks of FIG. 3 after aluminum deposition, sharpening and thick-film printing and firing of successive layers including electrically insulative dielectric layer, electrically conductive leads, one or more electrically resistive heating elements and electrically insulative dielectric overcoat layer.

In a preferred embodiment, a first electrically insulative dielectric layer 242a is thick-film printed over most of the lateral surface area of the sharpened blade substrate 143 on the side of the sharpened blade substrate 143 coated with a thin layer of aluminum as seen in FIGS. 5 and 6. Following printing, this first layer of dielectric thick-film ink is fired in an air oven (e.g., at 510 C).

Next, while sharpened blade substrate 143 is still located within a cavity of the setter, a second electrically insulative dielectric layer 242b is thick-film printed over the fired first layer of dielectric in order to minimize the possibility of any small sites (i.e., commonly referred to as "pin-holes") that were not fully covered with the first layer of electrically insulative dielectric. Following printing, this second layer of dielectric thick-film ink is fired in an air oven (e.g., at 510 C).

Figure 7:
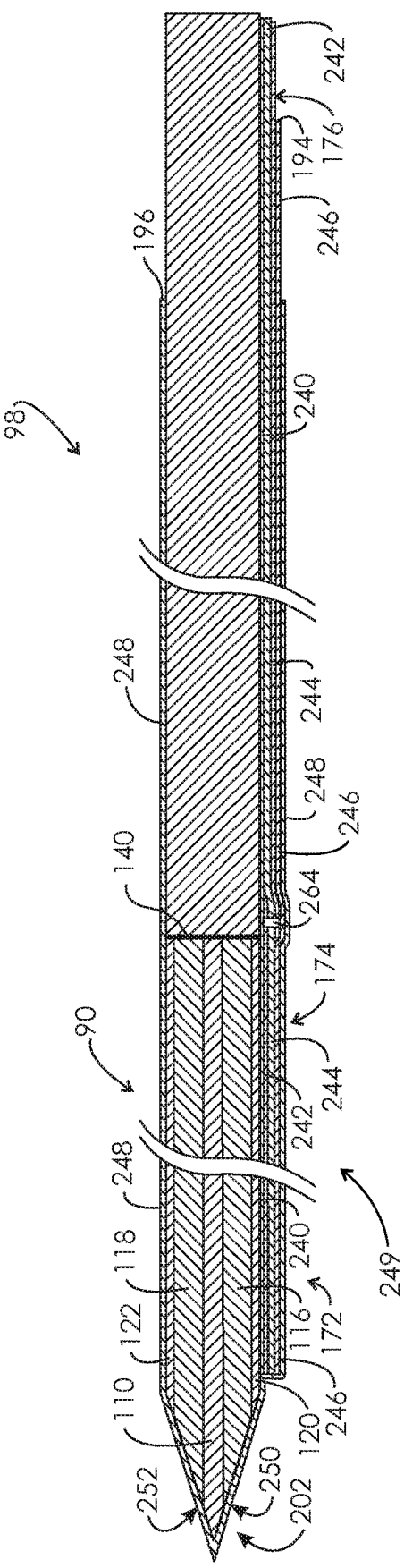
FIG. 7 is a sectional view taken through line of 7-7 of FIG. 5 showing five-layer laminate region and solid stem material of sharpened blade substrate on which is successively disposed an aluminum layer, an electrically insulative dielectric layer, an electrically conductive lead layer, an electrically resistive heating element layer, an electrically insulative dielectric overcoat layer and a non-stick coating layer on the outer surface of the blade assembly.

Next, while sharpened blade substrate 143 is still located within a cavity of the setter, a third layer comprising an electrically conductive thick-film ink is next printed over the previously fired dielectric layers 242 to form electrically conductive leads 176-179, as seen in FIG. 5. Those leads 176-179 extend rearwardly to define the region of a terminal array represented generally at 182. The term "region of a terminal array" refers to the terminal array 182 of conductive leads 176-179 that extend proximal to boundary 194 of electrically insulative overcoat 246 as seen in FIG. 7. The electrically conductive leads 176-179 are thick-film printed on stem portion structure 98 of sharpened blade substrate 143 comprised of a low thermal conductivity stainless steel. The electrically conductive leads 176-179 extend from the vicinity of and distal to the weld zone to the proximal end of the sharpened blade substrate 143. Following printing, this third layer of an electrically conductive thick-film ink is fired in an air oven, preferably at a temperature lower (e.g., at a temperature of 450 C) than the firing temperature employed for the dielectric layers to prevent migration of the electrically conductive thick-film ink layers through the electrically insulative dielectric layers 242.

Referring to FIGS. 5, 6 and 7, while sharpened blade substrate 143 is still located within a cavity of the setter, a fourth layer comprising an electrically resistive thick-film ink is next printed over the previously fired dielectric layers 242 to form one or more electrically resistive heating elements 171 (e.g., first or tip serpentine electrically resistive heating element segment 172 and second or heel serpentine electrically resistive heating element segment 174) on that portion of the sharpened blade substrate 143 comprised of the thermally conductive laminar cutting portion structure 90. The thick-film printed electrically resistive heating element material 173 exhibits a temperature coefficient of resistance of at least 0.0005Ω/° C. over temperature ranges of about 20° C. to about 300° C. As seen in FIGS. 5 and 7, the terminals 186-189 of the first or tip serpentine electrically resistive heating element segment 172 and second or heel serpentine electrically resistive heating element segment 174 are printed over the corresponding distal terminals of conductive leads 176-179 in region 264 to provide electrical communication between electrically resistive heating element 172, as well as electrically heating element 174 and the conductive leads 176-179, the electrical communication located on that portion of the sharpened blade substrate 143 comprised of the thermally conductive laminar cutting portion structure 90. The thick-film printed electrically resistive heating element material comprising electrically resistive heating elements 171 exhibits a temperature coefficient of resistance of at least 0.0005Ω/° C. over temperature ranges of about 20° to about 300° C. As seen in FIGS. 5 and 7, terminals 186-189 of one or more electrically resistive heating elements 172 and 174 are printed over the corresponding distal terminals of conductive leads 176-179 in region 264 to provide electrical communication between the electrically resistive heating elements 172 and 174 and the corresponding conductive leads 176-179. Following printing, this fourth layer of an electrically resistive thick-film ink is fired in an air oven, preferably at a temperature lower (e.g., at a temperature of 450 C) than the firing temperature employed for the dielectric layers to prevent migration of either the electrically resistive thick-film ink layer or the conductive lead thick-film lead layer through the electrically insulative dielectric layers 242.

Still referring to FIGS. 5, 6 and 7, a fifth thick-film printing and firing step is performed while sharpened blade substrate 143 is still located within a cavity of the setter. In this final thick-film printing step, a fifth layer of an electrically insulative dielectric overcoat 246 is thick-film printed over the previously printed and fired electrically resistive heating element layer 244 and electrically conductive leads 176-179 except in the proximal portion of the lead pattern intended to electrically communicate with corresponding electrical contacts (not shown) within the handle as defined by boundary 194. As seen in FIGS. 6 and 7, electrically insulative dielectric overcoat 246 terminates rearwardly at dashed termination line 194 to permit electrical communication of electrically conductive leads 176-179 with corresponding electrical contacts (not shown) in handle 16 seen in FIG. 1. Following printing, this fifth layer of an electrically insulative thick-film ink is fired in an air oven, preferably at a temperature lower (e.g., at a temperature of 450 C) than the firing temperature employed for the original electrically insulative dielectric layers to prevent migration of the previously printed electrically conductive and electrically resistive thick-film ink layers through the adjacent electrically insulative dielectric layers.

After multiple thick-film layers have been deposited on a sharpened blade substrate 143 substrate and fired, the thick-film printed sharpened blade substrate 143 assemblage is referred to as a surgical blade 12. Referring to FIGS. 5, 6 and 7, following the thick-film printing and firing process steps described in the preceding paragraphs including deposited one or more electrical resistance heating elements (e.g., first or tip serpentine electrically resistive heating element segment 172 and second or heel serpentine electrically resistive heating element segment 174), conductive leads 176-179 and electrically insulative dielectric overcoat 246, a non-stick coating 248 is deposited on those distal portions of the surgical blade 12 that may come in contact with tissue 216 during use in surgery as blood vessel 218 is transected as seen in FIG. 6 The portions of the surgical blade 12 on which non-stick coating 248 is deposited exclude the proximal portion of the lead pattern intended for electrical communication with corresponding electrical contacts (not shown) within the handle 16 seen in FIG. 1. A substantial portion of the surgical blade 12 is coated with a nonstick liquid coating that is cured and extends rearwardly on each side of surgical blade 12 to a location represented by dashed non-stick-coating termination line 196 as seen in FIGS. 5 and 7.

As seen in FIGS. 6 and 7, the surgical blade 12 has a laminar cutting portion structure represented generally at 90 that includes a cutting edge 198 and a faceted cutting edge region represented in general at 202. As seen before in FIG. 3, laminar cutting portion structure 90 is edge welded as represented by weld line 140 to stem portion structure represented generally at 98. Stem portion structure 98 is formed of an austenitic stainless steel such as type 304 that advantageously exhibits a low thermal conductivity.

In a preferred embodiment and referring to FIGS. 6 and 7, the thickness of the deposited non-stick coating 248 is sufficiently thin to eliminate the need for wiping of the portion of the blade facets that are within about 0.005 inch of the tip of the cutting edge of the surgical blade 12 to remove the non-stick coating from this cutting edge region 202 as previously required for non-stick coatings having a deposited thickness in the range from 0.0005 to 0.0010 inch. By way of example, the non-stick coating 248 may be deposited on the tissue-contacting surfaces of surgical blade 12 using a spraying process and cover the entire surface of the laminar cutting portion structure 90 and distal regions of the stem portion structure 98 while excluding the region of terminal array 182. After the deposition process, the non-stick coated surgical blade 12 is heated in an air oven at an elevated temperature (e.g., 330 C) for a short period (e.g., 15 minutes) during which the non-stick coating 248 is dried and adhered to the surface of surgical blade 12. In a preferred embodiment, the thickness, $t_7$ of the adhered non-stick coating 248 seen in FIGS. 5, 6 and 7 is less than 0.0001 inch and more preferably not greater than 0.00005 inch. Advantageously, the application of a non-stick coating such as ShieldSys SB (Miller Stephenson Chemical Company, Danbury, Connecticut) having a concentration of 20% and an adhered thickness of less than 0.0001 inch reduces the thermal resistance of non-stick coating 248 by a factor of about 10× as compared with conventional non-stick coatings such as Xylan 8110 (Whitford Corporation, West Chester, Pennsylvania) having a final adhered thickness of 0.0005 inch to 0.0010 inch. The preferred thickness of 0.00005 inch to 0.00010 inch for non-stick coating 248 corresponds to a preferred thermal resistance in the range from 0.05 to 0.10 C-$cm_2$/watt associated with heat conducted from the facets 250 and 252 of surgical blade 12 to the contacted tissue 216 being incised as seen in FIG. 6.

By way of example and still referring to FIG. 6, for the case of a preferred non-stick coating 248 having a thermal conductivity of 0.0025 watts/cm-C and thickness of 0.00005 inch, a corresponding thermal resistance of 0.05 C-$cm_2$/watt, a combined area of facets 250 and 252 in contact with tissue 216 during cutting equal to 0.3 $cm_2$ and 25 watts of heat conducted from facets 250 and 252 through the non-stick coating 248 into tissue 216, the calculated temperature difference across the preferred non-stick coating 248 is only 4.2 C. In contrast, the calculated temperature difference across a prior art non-stick coating having a thickness of 0.0006 inch would be 50.8 C. As a result of the significant lower thermal resistance of the preferred thinner non-stick coating 248, the amount of heat that would be conducted into tissue 216 from surgical blade 12 for a given operator selected set-point temperature (e.g., 250 C) will be greater thereby providing a greater degree of coagulation of incised tissue (i.e., a greater degree of hemostasis). Arrows 251 represent heat being transferred from surgical blade 12 into tissue 216.

Returning now to FIG. 1, following the deposition of non-stick coating 248 to the tissue-contacting surfaces of the surgical blade 12, the proximal portion of the surgical blade 12 that does not contact tissue during surgical use may be mechanically and/or adhesively attached to a thermally insulative sleeve 50 (e.g., injection molded plastic body) that enables [a] grasping the proximal portion of the sharpened blade for the purposeful step of insertion or removal of the sharpened blades from the handle while [b] avoiding physical contact with the sharpened cutting edge and/or the heated portion of the blade during the insertion or removal step.

Referring now to FIGS. 1 and 5, stem portion structure 98 may be configured with a rearward detent 208 located for engagement with a pawl engagement device within the handle 16 for the purpose of retaining surgical blade 12 within handle 16. Alternatively, magnetic retention may be used to retain surgical blade 12 within handle 16 by incorporating one or more permanent magnets (not shown) in the distal end of handle 16 and incorporating a ferromagnetic metal (e.g., carbon steel) insert (not shown) within sleeve 50 seen in FIG. 1. As disclosed above in connection with FIGS. 1 and 5, detent 210 also may be utilized to engage and retain sleeve 50.

The range of preferred dimensions for surgical blade 12, including its multiple deposited layers, are listed below where dimensions are in units of inches unless noted otherwise.

$W_1$=0.8 to 1.5
$W_2$=1.2 to 2.0
$W_3$=2.2 to 3.5
$W_4$=0.20 to 0.50
$t_1$=0.005 to 0.010
$t_2$=0.010 to 0.025
$t_3$=0.010 to 0.025
$t_4$=0.001 to 0.003
$t_5$=0.027 to 0.063
$t_6$=0.0002 to 0.0020
$t_7$=0.00005 to 0.00010
$\Phi$=21 to 25 degrees
$L_1$=18 to 36
$L_2$=2 to 4
$L_3$=4 to 6
$L_4$=0.6 to 1.2

The manufacturing process for forming blades according to the preferred embodiment disclosed in connection with FIGS. 2-7 is set forth in the flow chart represented in FIGS. 8A-8D. Those figures should be considered as labeled thereon. Looking to FIG. 8A, the procedure commences with the roll bonding of three materials to form a five-layer laminate as described at block 300. Those three materials are an annealed, cutlery-grade metal (by way of example, martensitic stainless steel) as represented at block 302 and arrow 304. This material exhibits a high hardness and high mechanical strength and is provided, for example, as stainless steel type 440C or 420C, Hitachi Metal GIN-4 or GIN-5 or Sandvik 13C26. An important advantage of the utilization of such material as a laminate core resides in the fact that it can be heat treated to elevate the level of its hardness. By way of example and also referring to FIG. 2, the hardness of the core material may be increased to 60 to 63 Rc (i.e., Rockwell C scale). As seen in FIG. 4A, the resulting cutting edge 198 of sharpened blade substrate 143 formed from a core 110 having a hardness of 60 to 63 Rc can be made sharper and will retain its sharpness for a longer interval of surgical use.

Still referring to FIG. 8A, as well as FIG. 2, another unique feature of this symmetrical five-layer laminate resides in the utilization of annealed layers (116, 118) of a metal exhibiting high thermal conductivity, for example, layers 116, 118 of an oxygen-free high conductivity (OFHC) copper as identified at block 306 and arrow 308. In this regard, strips of copper of identical thicknesses are roll bonded to the oppositely disposed faces 112, 114 of the core material, 110 having a finished thicknesses (after roll bonding) of $t_2$ and $t_3$.

Lastly, the copper strips are supported by a buttressing layer of high mechanical strength material roll bonded to the outwardly disposed surfaces thereof. As before, to achieve requisite symmetry, those buttressing strips are of equal thickness having a finished thickness (after roll bonding) of $t_4$. As represented at block 310 and arrow 312 of FIG. 8A, the buttressing strips may be provided as an annealed austenitic stainless steel such as a type 301 or 304. The roll bonding, as represented at block 300, is a process that produces a metallurgical bond as the lattice structures of the metals involved are forced into conformance with each other. High pressure, producing massive deformation of the metals, causes the sharing of electrons at the interface that produces a bond on the atomic level. No intermediate layers such as adhesives or brazing metals are involved. Roll bonding services are provided, for instance, by Polymetallurgical Corporation of North Attleboro, Massachusetts The resultant symmetrical laminar cutting portion structure 90 has been described in FIGS. 2, 3 and 4A as first strip 132 (after trimming). As represented at arrow 314 and block 316, this as-rolled laminated five-layer strip is trimmed to a desired width, W1. Depending upon the required cutting length, $L_4$ as seen in FIG. 4 the width of first strip 132 will generally be in the range from about 0.8 inch to about 1.5 inch to provide a symmetrical five-layer laminar cutting portion structure 90 having a thickness of about 0.027 inch to about 0.063 inch. As noted above, because of the symmetrical design in terms of materials utilized and thicknesses there is an assurance that, while some differential expansion forces will be encountered, they are evenly disposed on either side of the martensitic stainless steel core 110, thereby minimizing any warpage.

As represented at arrow 318 and block 320 of FIG. 8A, stem portion structure 98 material of low thermal conductivity and appropriate strength is provided. In this regard, an austenitic type 304 stainless steel second strip 138 as described in FIG. 3 may be provided. That stainless steel second strip 138 may be, for example, between about 1.2 inch and 2.0 inch in width and will have a thickness corresponding with the thickness of first strip 132 corresponding to laminar cutting portion structure 90. In general, an electron beam welding process may be employed to produce this composite sheet 130 seen in FIG. 3. The resultant weld line has been described at 96 in FIGS. 2 and 3A and the combination of first strip 132 and second strip 138 is described as a dual-metal laminate or composite strip 130.

Next, as represented at arrow 322 and block 324 of FIG. 8A, the dual-metal laminate or composite sheet 130 is cut into strips with a length, $L_1$ that is suitable for electro-discharge machining. The result, as described in connection with FIG. 3, is a quadrilateral composite sheet 130 with oppositely disposed widthwise sides arranged at a 45° angle and exhibiting a length, $L_1$, for example, of 20 inches. Such sloping sides have been described in FIG. 3 at 134 and 136. Additionally, as represented at arrow 326 and block 328, a hole is drilled in a corner of the type 304 stainless steel stem portion second strip 138 of the composite sheet 130 for use in hanging composite sheet 130 in a vertical orientation within a furnace during heat treatment to avoid any warpage or distortion from a flat configuration. That hole has been described at 144 in FIG. 2.

Figure 8B:
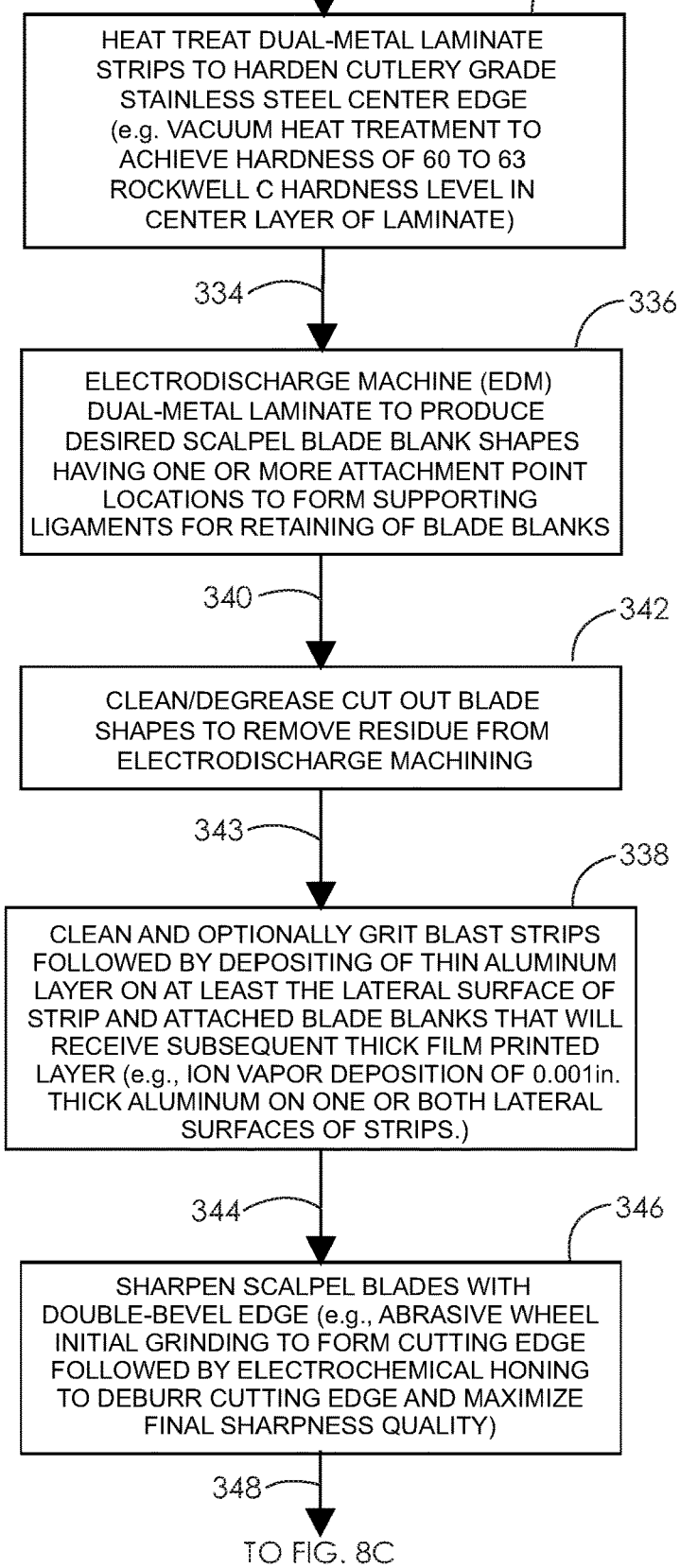

Next, as represented at arrow 330 and block 332 of FIG. 8A, the dual-metal laminate or composite sheet 130 is heat treated in order to increase the hardness of its martensitic stainless steel core 110. As represented at block 332, this heat treatment process may be performed in an evacuated heat treatment furnace (i.e., vacuum furnace) to advance the hardness of that core to a Rockwell C value of about 60 to 63. Such a vacuum furnace increases the temperature of composite sheet 130 to about 1000 C that is within about 80 C of the melting point of the copper layers 116 and 118 within the laminar cutting portion structure 90. Hardness is achieved with a subsequent rapid cool down of the composite strip 130. For example, cool down of the composite strip 130 by back filling the evacuated furnace with a non-oxidizing gas such as nitrogen. With such a heat treatment process, as represented at arrow 330 and block 332 of FIG. 8B, a composite strip is produced having a sufficiently high level of hardness as required for subsequent sharpening process steps.

Next, as represented at arrow 334 and block 336 of FIG. 8B, a multiplicity of heat-treated composite sheets 130 are arranged in a stack of 20 to 40 composite sheets 130. The stacks of composite sheets 130 are cut within an electro-discharge machine (EDM) to develop the blade blanks as described, for example, at 142 in connection with FIG. 3. An EDM machining process is preferred relative to a die-stamping operation to avoid cracking within or damage to the hardened martensitic stainless steel core 110 of composite sheet 130. During the EDM cutting procedure, the composite sheets 130 are typically submerged within an electrically insulative oil bath.

The cutting of the composite sheets 130 to form blade blanks 142 is continued over most of the perimeter of blade blanks 142 leaving a small ligament (e.g., uncut length of 0.040 inch) so that the blade blanks 142 remain attached to composite sheets 130 during the subsequent deposition of aluminum on at least one side of composite sheet 130 as seen in FIG. 3. As represented at arrow 340 and block 342 of FIG. 8B, following the cutting of composite sheet 130 into defined blade blanks 142 that remain attached to composite sheet 130, each composite sheet 130 is cleaned and optionally grit blasted to prepare at least one of the side surfaces for aluminum deposition. The side surface of composite sheet 130 on which an aluminum layer is deposited is the same side surface upon which an insulative dielectric layer, one or more electrically resistive heating elements, electrically conductive leads and electrically insulative overcoat layer are sequentially thick-film printed and fired.

Next, as represented at arrow 343 and block 338 of FIG. 8B, a thin layer of aluminum is deposited on at least one side of composite strip 130. Importantly, the deposition of aluminum layer 240 is accomplished while the defined blade blanks 142 remain attached to composite sheet 130 to facilitate efficient aluminum coating process steps since one entire side of composite strip 130 can receive a deposited layer of aluminum resulting in the deposition of aluminum on multiple blade blanks 142 as seen in FIG. 3. As seen in FIGS. 3 and 3A, a thin aluminum layer 240 is deposited on the side surface of composite sheet 130, preferably, the thickness of the aluminum layer, $t_6$ is in the range from 0.0002 inches to 0.002 inches. The aluminum layer 240 is deposited at least on the same side surface of the blade blanks upon which an insulative dielectric layer, one or more electrically resistive heating elements, electrically conductive leads and electrically insulative overcoat layer are subsequently and sequentially thick-film printed and fired. Importantly, the aluminum within the aluminum layer 240 enables a chemical reaction with the thick-film electrically resistive dielectric layer, resulting in the secure bonding of commercially available, electrically insulative dielectric thick film inks that have been specially formulated for deposition on an aluminum heat sink substrate (e.g., light emitting diode heat sinks) and include thick film inks such as such as DuPont AS-100 available from DuPont Microcircuit Materials (Research Triangle Park, North Carolina) or Celcion IP6080 available from Heraeus Electronics (Hanau, Germany). By way of example, the aluminum layer 240 seen in FIG. 3A may be deposited by ion vapor deposition (e.g., Titanium Finishing Company located in East Greenville, Pennsylvania).

As represented at arrow 344 and block 346 of FIG. 8B, following the deposition of aluminum layer 240 on composite sheet 130 and in preparation for the sharpening process, the individual blade blanks 142 are separated from composite strip 130 by breaking or cutting the small ligaments that heretofore retained the blade blanks 142 within the composite strip 130. Next, the blade blanks 142 are sharpened with a double-bevel cutting edge 198 as seen in FIGS. 4 and 4A. The cutting edge 198 of sharpened blade substrate 143 is revealed, for example, in FIG. 4A wherein the included angle, Φ extending upwardly from cutting edge 198 is at about 20° to 24°, preferably 22°, in order to increase the level of sharpness of cutting edge 198. The sharpening of blade blanks 142 may be performed by mechanical grinding using an abrasive grinding wheel followed by a second step involving stropping the cutting edge 198 using a leather and/or cotton wheel to remove any burrs or metallic residues formed during the first mechanical grinding step. In a preferred third step, or in place of the aforementioned second stropping step, an electrochemical honing or deburring process may be used as the final step in the sharpening of each blade blank 142. Alternatively, the first step in blade sharpening may employ an electrochemical process wherein an electric current flows between a negatively charged abrasive wheel and the positively charged blade blank through an electrolyte (e.g., sodium chloride) solution. A chemical reaction action occurs forming an oxidized surface on the blade blank surface being sharpened. The oxidized surface is removed by the specially formulated abrasives in the wheel, thereby exposing more material and repeating the cycle to form a sharp, burr-free cutting edge in a single step.

Figure 8C:
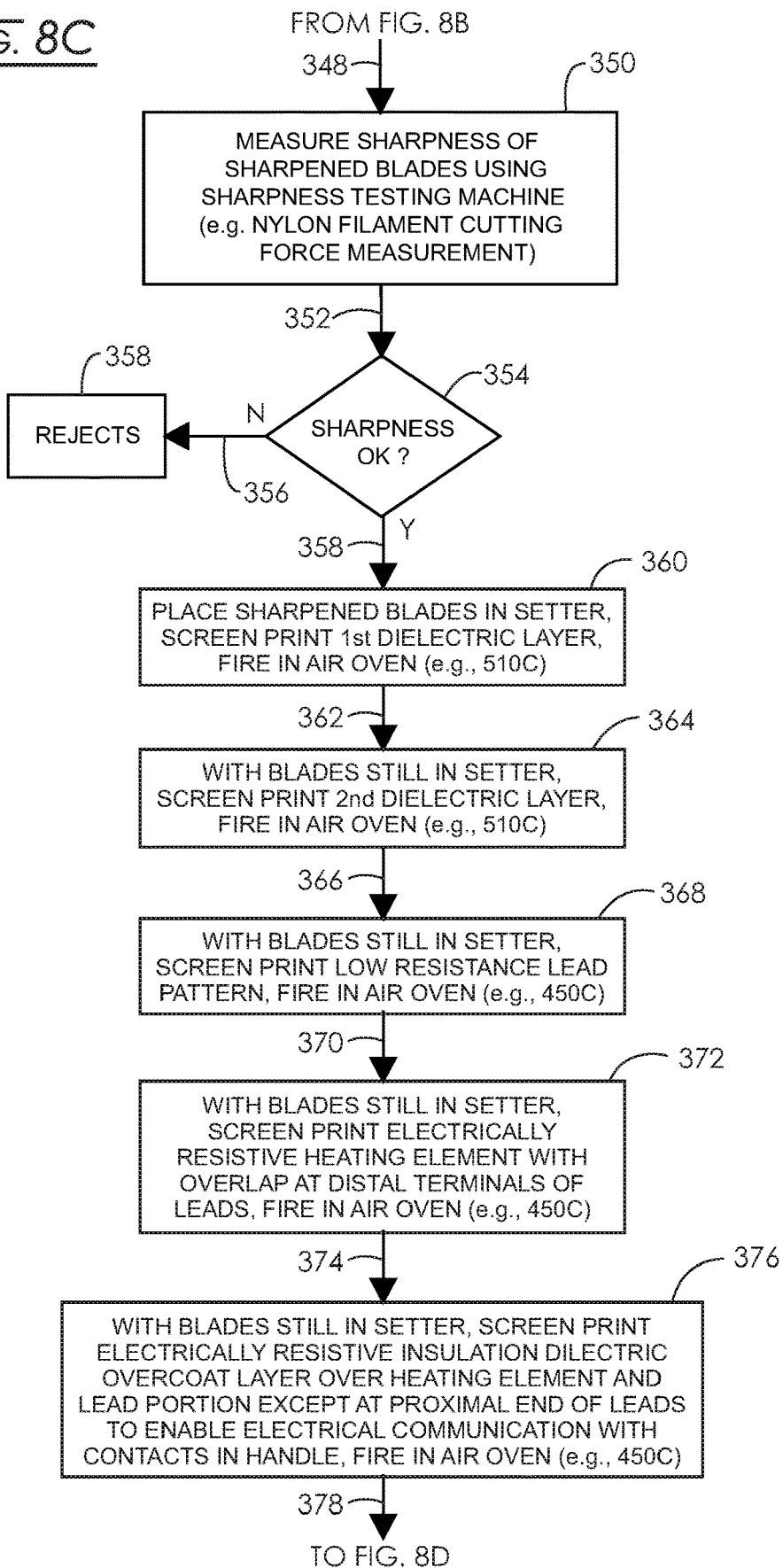

Next, as represented at arrow 348 and block 350 of FIG. 8C, initial non-destructive sharpness testing may be carried out, preferably on a sampling basis. Such testing may, for example, be performed by measuring the force required to cut through a water-saturated nylon filament at three different locations along the blade edge. This test may be performed on a sampling basis for a given lot of sharpened blade substrates 143, for example, 5-10% of the lot may be subjected to sharpness testing. Of course, sharpness testing may be performed on 100% of the lot of sharpened blade substrates 143. As represented at arrow 352 and block 354 of FIG. 8C, a determination is made as to whether the blades have met the sharpness criteria. In the event they have not, then as represented at arrow 356 and block 358 of FIG. 8C, the sharpened blade substrates 143 exhibiting inadequate sharpness are rejected.

On the other hand, where the sharpness test confirms sharpened blade substrates 143 exhibiting acceptable sharpness levels, then as represented at arrow 358 and block 360 of FIG. 8C, a multiplicity of sharpened blade substrates 143 with acceptable sharpness are placed in a fixturing plate or setter for use in subsequent thick-film printing and firing. The fixturing plate or setter is fabricated from a metal (e.g., titanium or titanium alloy) that is oxidation resistant and suitable for repeated exposure to temperatures of up to 550 C in air without oxidation, without reaction with materials within sharpened blade substrate 143 and that is resistant to distortion or warping. As seen in FIG. 4, the multiplicity of sharpened blade substrates 143 are accurately positioned within a thick-film printing fixture or setter (not shown) utilizing registration detents 208 and 210 in combination with upper edge 192 of sharpened blade substrate 143. The position of the machined cavities on the on the top surface of the setters are accurately positioned to align with the thick-film printing screens used to screen print multiple layers of dielectric, resistor and conductor thick-film inks. Following solvent cleaning of the upper surface of sharpened blade substrates 143 while positioned within the setter, the setter and sharpened blade substrates 143 are placed in an oven to remove any liquid residue dry in an air oven at about 400 C. Following cleaning and drying of the upper surface of each sharpened blade substrate 143 as seen in FIG. 4, a succession of thick-film printing and firing steps are sequentially performed to deposit one or more electrically insulative dielectric layers, electrically resistive heating element, electrically conductive leads and electrically insulative dielectric overcoat layer. The thick-film printing and firing of each of these successive layers is described in greater detail below in connection with FIGS. 5, 6 and 7.

As seen in block 360 of FIG. 8C, a first electrically insulative dielectric layer 242 is thick-film printed over most of the lateral surface area of the sharpened blade substrate 143 on the side of the sharpened blade substrate 143 coated with a thin layer of aluminum as seen in FIG. 4. Following printing, this first layer of dielectric thick-film ink is fired in an air oven (e.g., at 510 C).

Next, as represented at arrow 362 and block 364 of FIG. 8C, while sharpened blade substrate 143 is still located within a cavity of the setter, a second electrically insulative dielectric layer 242 is thick-film printed over the fired first layer of dielectric in order to minimize the possibility of any small sites (i.e., commonly referred to as "pin-holes") that were not fully covered with the first layer of electrically insulative dielectric. Following printing, this second layer of dielectric thick-film ink is fired in an air oven (e.g., at 510 C).

Next, as represented at arrow 366 and block 368 of FIG. 8C, while sharpened blade substrate 143 is still located within a cavity of the setter, a third layer comprising an electrically conductive thick-film ink is next printed over the previously fired dielectric layers 242 to form electrically conductive leads 176-179, as seen in FIG. 5. Those leads 176-179 extend rearwardly to define a terminal array represented generally at 182. The electrically conductive leads 176-179 are thick-film printed on stem portion structure 98 of sharpened blade substrate 143 comprised of a low thermal conductivity stainless steel that extends from the vicinity of and distal to the weld zone to the proximal end of the sharpened blade substrate 143. Following printing, this third layer of an electrically conductive thick-film ink is fired in an air oven, preferably at a temperature lower (e.g., at a temperature of 450 C) than the firing temperature employed for the dielectric layers to prevent migration of the electrically conductive thick-film ink layers through the electrically insulative dielectric layers 242.

Referring to FIGS. 4, 5, 6 and 7 and as represented at arrow 370 and block 372 of FIG. 8C, while sharpened blade substrate 143 is still located within a cavity of the setter, a fourth layer comprising an electrically resistive thick-film ink is next printed over the previously fired dielectric layers 242 to form one or more electrically resistive heating elements 171 (e.g., first or tip serpentine electrically resistive heating element segment 172 and second or heel serpentine electrically resistive heating element segment 174) on that portion of the sharpened blade substrate 143 comprised of the thermally conductive laminar cutting portion structure 90. As seen in FIGS. 4 and 7, the terminals 186-189 of the one or more electrically resistive heating elements 171 are printed over the corresponding distal terminals of conductive leads 176-179 in region 264 to provide electrical communication between the one or more electrically resistive heating elements 171 and corresponding conductive leads 176-179. Following printing, this fourth layer of an electrically resistive thick-film ink is fired in an air oven, preferably at a temperature lower (e.g., at a temperature of 450 C) than the firing temperature employed for the dielectric layers to prevent migration of either the electrically resistive thick-film ink layer or the conductive lead thick-film lead layer through the electrically insulative dielectric layers 242.

Still referring to FIGS. 4, 5, 6 and 7 and as represented at arrow 374 and block 376 of FIG. 8C, a fifth thick-film printing and firing step is performed while sharpened blade substrate 143 is still located within a cavity of the setter. In this final thick-film printing step, a fifth layer of an electrically insulative dielectric overcoat 246 is thick-film printed over the previously printed and fired electrically resistive heating element layer 244 and electrically conductive leads 176-179 except in the proximal portion of the lead pattern intended to electrically communicate with corresponding electrical contacts (not shown) within the handle as defined by boundary 194. As seen in FIGS. 6 and 7, electrically insulative dielectric overcoat 246 terminates rearwardly at dashed termination line 194 to permit electrical communication of electrically conductive leads 176-179 with corresponding electrical contacts (not shown) in handle 16 seen in FIG. 1. Following printing, this fifth layer of an electrically insulative thick-film ink is fired in an air oven, preferably at a temperature lower (e.g., at a temperature of 450 C) than the firing temperature employed for the original electrically insulative dielectric layers to prevent migration of the previously printed electrically conductive and electrically resistive thick-film ink layers through the adjacent electrically insulative dielectric layers.

Referring to FIGS. 5, 6 and 7 and as represented at arrow 378 and block 380 of FIG. 8D, following the thick-film printing and firing process steps described in the preceding paragraphs, surgical blade 12, with deposited one or more electrical resistance heating elements 171, conductive leads 176-179 and electrically insulative dielectric overcoat 246, a very thin non-stick coating 248 is deposited on those distal portions of surgical blade 12 that may come in contact with tissue 216 during use in surgery. By way of example, as seen at arrow 381 and block 383 of FIG. 8D, the non-stick coating may be a liquid coating known as ShieldsSys SB coating, 20% concentration, available from Stephens Chemical Company, Danbury, Connecticut The portions of the surgical blade 12 on which non-stick coating 248 is deposited exclude the proximal portion of the lead pattern intended for electrical communication with corresponding electrical contacts (not shown) within the handle 16 seen in FIG. 1. A substantial portion of the surgical blade 12 is coated with a nonstick liquid coating 248 that is cured and extends rearwardly on each side of the blade to a location represented by dashed non-stick-coating termination line 196 seen in FIG. 7.

Following application of the non-stick coating 248, as represented at arrow 382 and block 382 of FIG. 8D, the ShieldsSys SB non-stick coating 248 is cured in an air oven, for 15 minutes at 330° C. for five minutes in air.

Following curing as described in connection with block 384, two tests of the resultant heating circuit of surgical blade 12 are carried out. As represented at arrow 390 and block 392, heater segment resistance is tested. For an associated controller to perform employing auto-calibration, that resistance, for example, should be in a range from 4.0 ohms to 6.0 ohms. Accordingly, resistance values outside of this range will represent an open circuit or short circuit condition. Under those conditions, the blades are rejected and 100% of the blades are put under this resistance test. Accordingly, as represented at arrow 394 and block 396, a query is made as to whether blade resistance is within the noted range. Where it is not, then as represented by arrow 398 and block 400, the blade is rejected. On the other hand, where the blade passes this resistance test, then as represented at arrow 402 and block 404, a power application test is carried out to check ability of the tip and heel resistive heater segments to withstand full power application during use in surgery. In this regard, the resistive heater segments may exhibit a narrowed or thinned out portion or partially cracked portion. Under a ramping-up power application such defects will cause the resistive heater segments to fail. Accordingly, 100% of the blades must pass this test. As represented at arrow 406 and block 408, a query is made as to whether a given surgical blade 12 has passed the power-up test. In the event that it has not, then as represented at arrow 410 and block 412, the surgical blade 12 is rejected. Where the power-up test is passed, then, as represented at arrow 414 and block 416, sterilization and packaging procedures are undertaken. Sterilization may be, for example, by gamma radiation impingement or ethylene oxide. Following packaging, as represented at arrow 418 and block 420, the packaged and sterilized blades are placed in finished goods inventory and, as represented at arrow 422 and block 424, ultimately the packaged blades are shipped to a customer.

While the apparatus, system, and method have been described with reference to various embodiments, those skilled in the art will understand that various changes may be made and equivalents may be substituted for elements thereof without departing from the scope and essence of the disclosure. In addition, many modifications may be made to adapt a particular situation or material in accordance with the teachings of the disclosure without departing from the essential scope thereof. Therefore, it is intended that the disclosure not be limited to the particular embodiments disclosed, but that the disclosure will include all embodiments falling within the scope of the appended claims. In this application all citations referred herein are expressly incorporated herein by reference.

The invention claimed is:

1. A surgical blade (12) for a hemostatic surgical instrument (10) comprising:
 (a) a laminar cutting portion structure (90) having:
  (i) a core (110) of cutlery-grade metal and having sides, an adjacent cutting edge region (202), and a blade surface (239);
  (ii) oppositely disposed layers of a metal exhibiting a high thermal conductivity (116, 118) and bonded in thermal exchange relationship on the core sides and having outwardly disposed surfaces (117, 119);
  (iii) buttressing layers of high mechanical strength material (120, 122) and being bonded to the outwardly disposed surfaces (117, 119) to form a blade blank (142) having sides;

(iv) an aluminum layer (240) deposited on one side of the blade blank (142) that enables chemical reaction bonding to a thick-film printed dielectric layer (242); and (v) one or more thick-film printed and fired electrically resistive heating elements (171) deposited on the aluminum layer and being in thermal exchange relationship with the oppositely disposed layers (116, 118);

(b) a stem portion structure (98) formed of low thermal conductivity material, the stem portion having a proximal end edge welded to the laminar cutting portion structure (90) and having a distal end configured to be supported by a handle; and (c) a blade heating circuit (249) deposited on the aluminum layer and in electrical communication with electrically conductive leads (176-179) deposited on the stem portion structure (98) and forming a terminal array (182) at the stem portion structure distal end, the electrically conductive leads extending from the terminal array to the one or more thick-film printed and fired electrically resistive heating elements.

2. The surgical blade (12) of claim 1, wherein the blade heating circuit (249) comprises an electrically insulative dielectric layer (242) supporting an electrically resistive heating element layer (244) and electrically conductive leads (176-179) with an electrically insulative dielectric overcoat (246) covering the electrically resistive heating element and electrically conductive leads except at the location of the terminal array (182).

3. The surgical blade of claim 1, wherein the aluminum layer is deposited using an ion vapor deposition process.

4. The surgical blade of claim 1, wherein the thickness of aluminum layer (240) is in the range from 0.0002 to 0.0020 inch.

5. The surgical blade of claim 1 further comprising:
a non-stick coating (248) deposited on the laminar cutting portion structure and regions of the stem portion structure (98) that are distal to the region of the terminal array (182).

6. The surgical blade of claim 5, wherein the thickness of non-stick coating (248) is not greater than 0.0001 inch.

7. The surgical blade of claim 5, wherein the thickness of non-stick coating (248) is not greater than 0.00005 inch.

8. The surgical blade of claim 5, wherein a thermal resistance of the non-stick coating (248) does not exceed 0.10 C/watt-cm$^2$.

9. The surgical blade of claim 1, wherein the blade heating circuit (249) with one or more resistive heating elements (171) comprise a thick-film printed electrically resistive heating element material exhibiting a temperature coefficient of resistance of at least 0.0005 0/° C. over temperature ranges of about 20° C. to about 300° C.

10. The surgical blade of claim 1, wherein the stem portion structure (98) is formed having a length effective to surgically access tissue within a body cavity; and further comprising a thermally insulative sleeve (50) surmounting at least a portion of the stem portion structure.

11. The surgical blade of claim 1, wherein the laminar cutting portion structure comprises a cutting edge region (202) having a double facet (250, 252) with an included angle of about 22 degrees.

12. The surgical blade of claim 1, wherein the oppositely disposed layers (116, 118) are formed of oxygen-free high conductivity (OFHC) copper roll bonded to the oppositely disposed faces (112, 114) of core material (110).

13. The surgical blade of claim 1, wherein the cutlery-grade metal of the core (110) is martensitic stainless steel.

14. The surgical blade of claim 1, wherein the core (110) additionally comprising:

(d) a handle (16) attached to the distal end of stem portion structure (98) wherein the stem portion structure (98) formed of a low thermal conductivity material limits the amount of heat that is conducted from the laminar cutting portion structure (90) to the handle (16) during surgical use when surgical blade (12) is operating at an elevated temperature.

15. The method of manufacturing a surgical blade (12) having a laminar cutting portion structure (90) and a stem portion structure (98), comprising the steps:

(a) providing a cutlery grade metal core (110) of cutlery-grade metal having a widthwise extent effective for forming the laminar portion structure and a thickness defined between oppositely disposed faces (112, 114) of the cutlery grade metal core;

(b) providing oppositely disposed layers of a metal exhibiting a high thermal conductivity (116,118) and roll bonding the oppositely disposed layers of a metal exhibiting a high thermal conductivity to the oppositely disposed cutlery grade metal core faces, the roll bonded oppositely disposed layers and oppositely disposed cutlery grade metal core faces being in thermal exchange relationship, the bonded disposed layers having surfaces (117, 119);

(c) providing two stainless steel layers (120, 122) of high mechanical strength material and having a shape corresponding with the shape of the oppositely disposed layers of a metal exhibiting a high thermal conductivity;

(d) roll bonding a stainless steel layer (120, 122) to the bonded disposed layers having surfaces in step (b) to provide a symmetrical, five-layer laminar cutting portion structure (90);

(e) providing a second strip (138) of metal exhibiting low thermal conductivity having a thickness corresponding to the thickness of the five-layer laminar cutting portion structure in step (d) and having a shape effective to form the stem portion structure;

(f) edge welding the second strip of metal exhibiting low thermal conductivity of step (e) to the five-layer laminar cutting portion structure in step (d) to provide a composite sheet (130);

(g) heat treating the composite sheet of step (f) to an extent effective to harden the cutlery grade metal core of cutlery-grade metal;

(h) forming cut blade blanks (142) within the heat treated composite sheet (130) of step (g), each cut blank having sides;

(i) depositing an aluminum layer (240) on at least one side of the heat treated composite sheet containing cut blade blanks of step (h) to enable chemical reaction bonding of the aluminum layer to a thick-film printed dielectric layer (242) of step (j);

(j) to the aluminum layer in step (i), printing and firing the thick-film electrically insulative dielectric layer (242), printing and firing the thick-film electrically resistive heating element layer (244); printing and firing thick-film electrically conductive leads (176-179) having a terminal array (182) to form an electrically resistive heating element (171), and printing and firing a thick-film electrically insulative dielectric overcoat (246)

covering the electrically resistive heating element and the electrically conductive leads except on the terminal array; and (k) sharpening the cutlery grade metal core of the cut blade blanks to define a double-bevel cutting edge (198) to form tissue-contacting surfaces.

16. The method of claim 15, further comprising the steps of:

(l) depositing a non-stick coating (248) on the tissue-contacting surfaces of surgical blade (12) using a spraying process and covering the entire surface of the laminar cutting portion structure (90) and the stem portion structure (98) while excluding deposition in the region of terminal array (182), (m) oven curing the deposited non-stick coating.

17. The method of claim 15, wherein layers (116,118) of a metal exhibiting a high thermal conductivity are provided as strips of oxygen-free high conductivity (OFHC) copper.

18. The method of claim 15, wherein the heat treating in step (g) is carried out in vacuum, non-oxidizing atmosphere or reducing atmosphere to an extent effective to harden the martensitic stainless steel core to a Rockwell C hardness of from about 60 to about 63.

19. The method of claim 15, wherein the sharpening in step (j) includes an electrochemical sharpening process.

20. The method of claim 15, wherein the sharpening in step (j) includes an electrochemical honing process.

21. The core (110) strip of cutlery-grade metal in claim 15, wherein the cutlery-grade metal is provided as a martensitic stainless steel.

* * * * *